(12) United States Patent
Kelly

(10) Patent No.: US 7,998,474 B2
(45) Date of Patent: Aug. 16, 2011

(54) METHODS FOR TREATING AN INFLAMMATORY DISEASE OF THE BOWEL

(75) Inventor: Denise Kelly, Kingswell (GB)

(73) Assignee: Rowett Research Institute, Bucksburn (GB)

( * ) Notice: Subject to any disclaimer, the term of this patent is extended or adjusted under 35 U.S.C. 154(b) by 0 days.

(21) Appl. No.: 10/285,224

(22) Filed: Oct. 31, 2002

(65) Prior Publication Data

US 2003/0133875 A1 Jul. 17, 2003

(30) Foreign Application Priority Data

Nov. 21, 2001 (GB) .................................. 0127916.5

(51) Int. Cl.
*A61K 35/74* (2006.01)
*A61P 29/00* (2006.01)
(52) U.S. Cl. ...................................... 424/93.4; 424/93.1
(58) Field of Classification Search .................. 424/93.4, 424/184.1, 780
See application file for complete search history.

(56) References Cited

U.S. PATENT DOCUMENTS

| | | | | |
|---|---|---|---|---|
| 5,039,703 | A * | 8/1991 | Breuer | 514/557 |
| 5,443,826 | A * | 8/1995 | Borody | 424/93.3 |
| 5,599,795 | A * | 2/1997 | McCann et al. | 424/93.4 |
| 5,925,657 | A | 7/1999 | Seed et al. | 514/369 |
| 5,951,977 | A * | 9/1999 | Nisbet et al. | 424/93.3 |
| 2004/0028689 | A1 * | 2/2004 | Borody | 424/184.1 |
| 2004/0062757 | A1 * | 4/2004 | Finegold | 424/93.45 |

FOREIGN PATENT DOCUMENTS

| | | |
|---|---|---|
| WO | WO 90 01335 | 2/1990 |
| WO | WO 98 43081 | 10/1998 |
| WO | WO 98 57631 | 12/1998 |
| WO | WO 99 45955 | 9/1999 |
| WO | WO 01 16120 | 3/2001 |

OTHER PUBLICATIONS

Rolfe. The role of probiotic cultures in the control of gastrointestinal health. J Nutr. 130(2S Suppl):396S-402S, Feb. 2000.*
Male, "Cell Migration and Inflammation" in Immunology, 4th ed. Mosby, 1998, pp. 14.1-14.9.*
Kelly et al. Commensal anaerobic gut bacteria attenuate inflammation by regulating nuclear-cytoplasmic shuttling of PPAR-gamma and RelA. Nat Immunol. vol. 5, No. 1, pp. 104-112, Jan. 2004.*
Yurduseve et al. Antagonistic effect exerted by three strictly anaerobic strains against various strains of *Clostridium perfringens* in gnotobiotic rodent intestines. Can J Microbiol. vol. 33, No. 3, pp. 226-331, Mar. 1987.*
Jax Mice Data Sheet, Strain Name: C3H/HeJ, Stock No. 000659, http://jaxmice.jax.org, viewed on Sep. 22, 2005.*
A.D.A.M. Medical Encyclopedia [Internet]. Atlanta (GA): A.D.A.M., Inc.; © 2005. Inflammatory bowel disease; [updated Jul. 19, 2004]. Available from http://www.nlm.nih.gov/medlineplus/ency/article/003247.htm.*
Ulcerative Colitis, National Digestive Diseases Information Clearinghouse, pp. 1-5, Feb. 2006, available at www.digestive.niddk.nih.gov.*
Crohn's disease National Digestive Diseases Information Clearinghouse, pp. 1-7, Feb. 2006, available at www.digestive.niddk.nih.gov.*
A.D.A.M. Medical Encyclopedia [Internet]. Atlanta (GA): A.D.A.M., Inc.; © 2005. Irritable bowel syndrome; [updated Jul. 16, 2004]. Available from http://www.nlm.nih.gov/medlineplus/ency/article/003247.htm.*
Steiner et al.Fecal lactoferrin, interleukin-1beta, and interleukin-8 are elevated in patients with severe *Clostridium difficile colitis*. Clinical and Diagnostic Laboratory Immunology, vol. 4, No. 6, pp. 719-722, Nov. 1997.*
Dongowski et al. Degradation of pectins with different degrees of esterification by *Bacteroides thetaiotaomicron* isolated from human gut flora. Applied and Environmental Microbiology, vol. 66, No. 4, pp. 1321-1327, Apr. 2000.*
Irian et al. The luminal short-chain fatty acid butyrate modulates NF-kappaB activity in a human colonic epithelial cell line. Gastroenterology, vol. 118, pp. 724-734, Apr. 2000.*
Tedelind et al. Anti-inflammatory properties of the short-chain fatty acids acetate and propionate: a study with relevance to inflammatory bowel disease. World Journal of Gastroenterology, vol. 13, No. 20, pp. 2826-2832, May 2007.*
Teng, L. J. et al., J Clin Microbiol 38, 1672-1675 (2000).
Lopez-Boado, Y. S. et al., J Cell Biol 148, 1305-1315 (2000).
Hooper, L. V. et al., Science 291, 881-884 (2001).
Neish, A. S. et al., Science 289, 1560 (2000).
Bry, L. et al., Science 273, 1380-1383 (1996).
Yurdusev, N. et al., Can J Microbiol 33, 226-231 (1987).
Yurdusev, N. et al., Infect Immun 57, 724-731 (1989).
International Search Report from PCT/GB02/05255 (mailed Mar. 15, 2003).

* cited by examiner

*Primary Examiner* — Jennifer Dunston
(74) *Attorney, Agent, or Firm* — Drinker Biddle & Reath LLP

(57) ABSTRACT

The invention relates to an assay to select a candidate drug for the treatment of inflammatory disease due to cytokine production. The assay comprises: a) exposing said candidate drug to intestinal cells; and b) analysing the effect of the said candidate drug selected from the group consisting of the variation of nuclear export or import of transcription factors from the NF-κB family the disruption of transcriptional activity of transcription factors from the NF-κB family, the differential histone acetylation of p65 (RelA); the variation of the amount of PPARγ/RelA complexes in the cytosol of the cells; and a combination thereof. The invention further relates to methods for the treatment of inflammatory cytokine production associated diseases and to the use of a therapeutically effective dose of *Bacteroides thetaiotaomicron* or a component thereof.

7 Claims, 13 Drawing Sheets

Fig. 9B    Northern blots
(example dose and time course data)
a
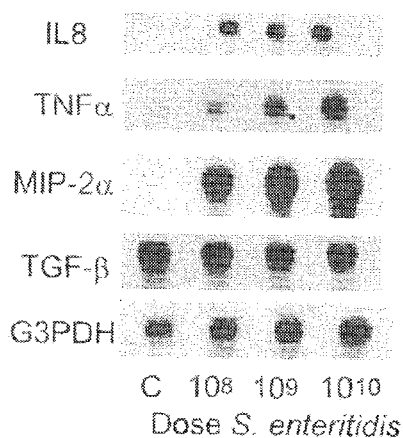
b
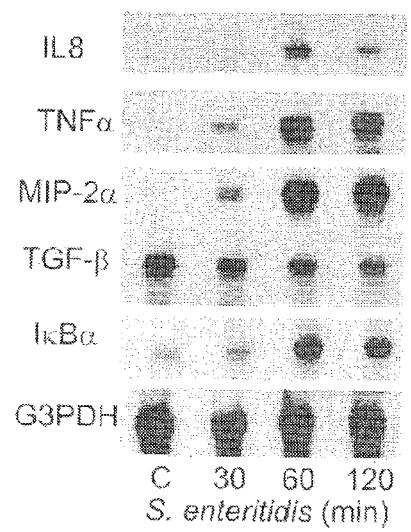
c
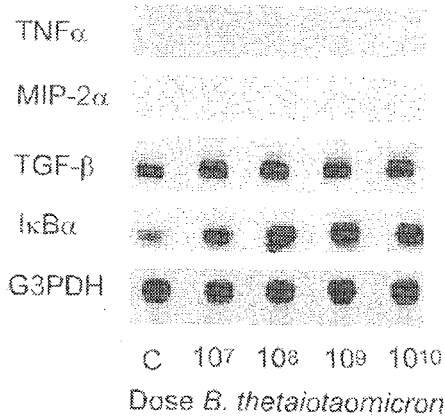
d
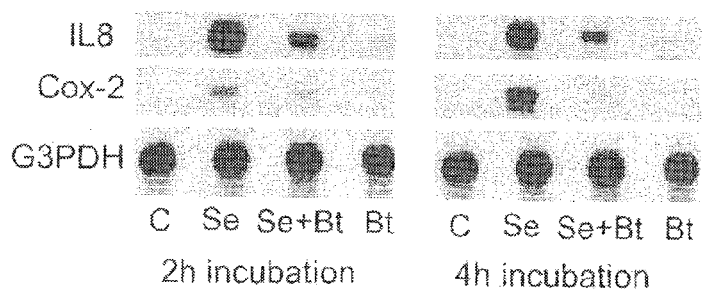

NFκB p65

Note: 2 hour data illustrated in manuscript

Note: 2 hour data illustrated in manuscript

Co-labelling of NFκB p65 and PPARγ in Caco2 cells following 2h exposure to *B. thetaiotamicron* and *S. enteriditis*

NFκB p65

2nd antibody conjugated to Alexa-Fluor 488 (green)

PPARγ

2nd antibody conjugated to Alexa-Fluor 568 (red)

NFκB p65
+
PPARγ

Dual channel image, regions of co-localization appear yellow.

METHODS FOR TREATING AN INFLAMMATORY DISEASE OF THE BOWEL

FIELD OF THE INVENTION

The present invention is concerned with modulating intestinal responses to infection, in particular through use of the bacterium *Bacteroides thetaiotaomicron*.

BACKGROUND OF THE INVENTION

The mammalian intestine is colonised by several hundred bacterial species whose numbers increase dramatically in the colon, an anatomical site prone to infection, inflammatory disease and cancer. However, the resident flora of the gastrointestinal tract of adult-animals conveys a high degree of protection (colonisation resistance) against infection (van der Waaij, 1984; Salminen et al, 1998). As a result, most opportunistic pathogens encountered in the environment are unable to establish a foothold and are rapidly excluded (van der Waaij, 1984; Salminen et al, 1998). However, if the commensal flora is compromised, opportunistic pathogens may then persist in the gut. For example, *Pseudomonas aeruginosa* does not usually persist in the murine gut but will colonise and cause very severe infection after disruption of the commensal flora with antibiotics (Pier et al, 1992). The commensal bacteria also confer some degree of protection against virulent pathogens, such as Salmonella. However, these pathogens can overwhelm or circumvent the protective effects of the commensal flora and cause severe infection if they are present in significant numbers.

Colonisation resistance is due, in part, to competitive exclusion of harmful bacteria, through preferential use of nutrients and substrates or blocking of potential attachment sites on the gut by the commensal flora. However, commensal bacteria also modulate the gut cellular and immune systems of the host (Bry et al, 1996; Herias et al, 1998; 1999; Hooper et al, 2000; 2001; Cebra, 1999; Snel et al, 1998; Talham et al, 1999; Lopez-Boado et al, 2000; Shu et al, 2000; Campbell et al, 2001). The flora may alter the gastrointestinal tract to create niche microenvironments that are well suited to them but not to other bacteria. Alternatively, they may modify epithelial cell responses to harmful bacteria (Campbell et al, 2001) and thereby attenuate changes that would facilitate colonisation and invasion.

The healthy gut maintains a hyporesponsive tone towards its diverse bacterial load, yet the presence of a threshold level of pathogenic bacteria is sufficient to activate transcriptional systems that rapidly upregulate proinflammatory gene expression in gut tissues. These transcription products then trigger a cascade of responses including the chemotaxis of polymorphonuclear (PMN) cells into the lamina propria of infected intestinal sites. Although these events are essential for bacterial clearance, they also cause tissue pathology that can exacerbate the symptoms of disease. The first point of contact for lumenal bacteria is a continuous layer of epithelial cells that both interfaces and segregates the gut immune system. The ability of intestinal epithelial cells to discriminate between pathogenic and non-pathogenic bacteria is crucial in averting harmful inappropriate responses to colonising bacteria and in maintaining gut health. This discriminatory function is imprinted in the systems of bacterial recognition and cell signalling. Recognition of bacterial cell surface structures is, in part, a function of Toll-like receptors expressed on apical and basolateral surfaces of epithelial cells, which trigger Nuclear Factor Kappa B (NF-κB)-mediated immune activation (Gerwirtz et al, 2001). Hitherto, receptor systems linked to immune-suppressor activities have not been identified.

Administration of the human commensal bacterium *B. thetaiotaomicron* to germ-free mice triggered expression of key genes linked to intestinal maturation and development of barrier function (Hooper et al, 2001). It also increased intestinal levels of Fucα1,2Galβ-glycans (Bry et al, 1996; Hooper et al, 2001) and matrilysin (Lopez-Boado et al, 2000). *B. thetaiotaomicron* was also found to modify the responses of epithelial cells to challenge in vitro with Salmonella (Campbell et al, 2001). In particular, there was suppression of some pro-inflammatory pathways (Campbell et al, 2001). Despite these potentially protective properties, *B. thetaiotaomicron* did not however increase the resistance of ex-germ free mice to infection by *Clostridium perfringens* serotype A (Yurdusev et al, 1989). Nonetheless, the pathogen was cleared from the gut if the mice were treated with *B. thetaiotaomicron* in combination with *Fusobacterium necrogenes* (Yurdusev et al, 1989) and non-pathogenic Clostridia strain CI (Yurdusev et al, 1986). This suggests that, although *B. thetaiotaomicron* alone can induce potentially protective changes in the gut, it may need to act in tandem with other commensal strains to significantly enhance overall resistance to infection.

SUMMARY OF THE INVENTION

In this invention we define a novel mechanism whereby non-pathogenic bacteria, normally colonising the human intestine, attenuate epithelial inflammatory gene expression by altering both the nucleocytoplasmic distribution of PPARγ and the transcriptional activity of (NF-κB).

Further, this invention relates to the use of non-pathogenic bacteria for the modulation of inflammatory responses. Still further, the invention provides evidence for differential histone acetylation of p65 (RelA) affecting IκBα-mediated export of RelA and for a novel mode of action for peroxisome proliferatot-activated receptors (PPARγ). In particular, the invention describes the attenuation of epithelial inflammatory gene expression by altering both the nucleocytoplasmic distribution of PPARγ and the transcriptional activity of NF-κB by use of non-pathogenic bacteria. Further the present invention provides a means of attenuating inflammation for treatment and prevention of disease and inflammatory disorders.

The novel pathway described in the present invention can be used to screen for novel methods and for novel products to modulate inflammatory cytokine production. Further, the present invention describes the use of a non-pathogenic bacteria in attenuating inflammatory cytokine production and returning the immune system to homeostasis.

The modulation of inflammatory cytokine production described herein differs from known publications in a number of aspects.

U.S. Pat. No. 5,925,657 describes an agonist of PPARγ. This agonist is thiazolidinedione, a chemical compound with a substituted aryl moiety attached to a thiozolidinedione nucleus. In the present invention, a non-pathogenic bacterium is used to attenuate the inflammatory response by directly activating PPARγ.

Neish et al, 2000 describe regulation of epithelial responses by inhibition of IκBα ubiquitination. The present invention differs from Neish et al, 2000 by using a different mode of action.

The invention provides a novel mechanism whereby non-pathogenic bacteria, normally colonising the human intestine, attenuate epithelial inflammatory gene expression by altering both the nucleocytoplasmic distribution of PPARγ and the transcriptional activity of NF-κB. The invention also provides evidence for differential histone acetylation of p65 (RelA) affecting IκBα-mediated export of RelA and for a novel mode of action for peroxisome proliferatot-activated receptors (PPARγ). This novel data provides the potential for devising novel means of, and novel products for, modulating inflammatory cytokine production.

In vivo validation of the results are also described.

The present invention provides an assay to select a candidate drug for the treatment of inflammatory disease due to cytokine production. The assay comprises:
a) exposing the candidate drug to intestinal cells; and
b) analysing the effect of the said candidate drug selected from the group consisting of:
the variation of nuclear export or import of transcription factors from the NF-κB family;
the disruption of transcriptional activity of transcription factors from the NF-κB family;
the differential histone acetylation of p65 (RelA);
the variation of the amount of PPARγ/RelA complexes in the cytosol of the cells; and
nucleoplasmic destruction of PPARγ.

The assay may further comprise a step of selecting a drug candidate which demonstrates at least one effect selected from the group consisting of:
the increase of nuclear export or the decrease of nuclear import of transcription factors from the NF-κB family;
the disruption of transcriptional activity of transcription factors from the NF-κB family;
the differential histone acetylation of p65 (RelA);
the increase of the amount of PPARγ/RelA complexes in the cytosol of the cells; and
nucleoplasmic destruction of PPARγ.

According to a preferred embodiment, the effect of the candidate drug which is analysed is the nuclear export of transcription factor from the NF-κB family or the variation of the amount of PPARγ/RelA complexes in the cytosol of the cells.

Desirably the intestinal cells may be in form of an intestinal cell line maintained in cell culture. Suitable cell lines include Caco-2 cell line. Alternatively the assay could be performed in vivo using a suitable animal, like a mammal (eg. mice).

Optionally the effect of said candidate drug on the inflammatory response may be determined through measurement of the levels of one or more of TNF-α, IL-8, MIP-2α and Cox-2, more particularly IL-8 and/or MIP-2α.

Optionally the assay may be conducted in the presence of known pathogenic bacteria, for example *Samonella* sp.

The present invention also provides a method for the treatment or to attenuate the inflammatory response of intestinal cells which comprises administering a therapeutically effective dose of *Bacteroides thetaiotaomicron* or a component thereof. The term "a component thereof" as used herein refers to any portion (protein, polypeptide, sugar, nucleic acid and the like) normally forming part of *B. thetaiotaomicron* and which is able to attenuate the immune response as described.

In more detail *B. thetaiotaomicon* or its components may be used to disrupt the NF-κB pathway and/or to inhibit the p65 (RelA) response and/or act as an excitor or inhibitor of PPARγ. *B. thetaiotaomicon* or its components may therefore be used for the treatment of inflammatory cytokine production associated diseases.

The *B. thetaiotaomicon* may be administered to a patient live by means of a foodstuff or suppository.

Thus, this invention describes methods by administration of a therapeutically effective dose of a micro-organism, like *B. thetaiotaomicon*, or part of micro-organism or compound capable of altering the nucleocytoplasmic distribution of PPARγ and transcriptional activity of NF-κB for attenuating or preventing or treating inflammatory cytokine production associated diseases or conditions including but not limited to; inflammatory bowel disease and diseases (particular mention may be made of Crohn's disease and Irritable Bowel Syndrome); rheumatoid arthritis; immunodeficiency syndrome; cachexia; multiple sclerosis, inhibition of proliferation of keratinocytes; inhibition of hyperproliferative and inflammatory disorders of the skin including but not limited to psoriasis and acne vulgaris. Further, the present invention describes a method of returning and maintaining the immune system of mammals to homeostatis.

For the prevention and treatment of conditions described herein, *B thetaiomicron* is preferentially delivered to the site of action in the gastrointestinal tract by oral administration in any appropriate formulae or carrier or excipient or diluent or stabilizer. Such delivery mechanisms may be of any formulation including but not limited to solid formulations such as tablets or capsules; liquid solutions such as yoghurt or drinks or suspensions. A preferential delivery mechanism is one that delivers the bacteria orally, preferably without harm through the acid environment of the stomach to the site of action within the intestine. Such bacteria may be given in conjunction with a prebiotic.

The invention also provides a novel mode of action of PPARγ and differential histone acetylation of p65 (RelA) affecting IκBα-mediated export of RelA for screening for specific ligands with the potential to modulate, either agonistically or antagonistically, inflammatory cytokine production via the novel pathway described herein.

The invention further provide a method for the treatment of inflammatory cytokine production associated diseases which includes the step of administering a therapeutically effective dose of a compound capable of altering the transcriptional activity of NF-κB or capable of increasing the amount of PPARγ/RelA complexes in the cell cytosol.

The invention further provide a method of returning and maintaining the immune system of mammals to homeostasis, which includes the step of administering a therapeutically effective dose of a compound capable of altering the transcriptional activity of NF-κB or capable of increasing the amount of PPARγ/RelA complexes in the cell cytosol.

We have found that the anti-inflammatory activity of *B. thetaiotaomicron* involves a totally novel mode of action, defined by accelerated NF-κB nuclear export and PPARγ-mediated sequestration in the cytosol. The experimental work (described in detail in the examples) was undertaken in three phases:
1) Inflammatory cytokine gene expression in Caco-2 cells following exposure to pathogenic/non-pathogenic bacteria. Data was obtained using cDNA macroarray, real-time PCR and Northern hybridisation analysis.
2) In vitro (Caco-2 transwell cultures) and in vivo (minimal flora rats) validation of the physiological relevance of the anti-inflammatory effects of *B. thetaiotaomicron*.
3) Analysis of NF-κB and AP-1 signal transduction pathways and the relationship between cytosolic RelA and PPARγ.

The experimental work performed shows that:
1) The main target of regulation by *B. thetaiotaomicron* is NF-κB and not AP-1.
2) p65 (RelA) accumulated in cells treated with *B. thetaiotaomicron* and *S. enteritidis* (detected up to 30 minutes).
3) The reduced transcriptional effects of p65 in the presence of *B. thetaiotaomicron* are due to an enhanced nuclear clearance (export) of p65, and this export is LMB sensitive (ie. crm −1 mediated).

4) The data correlated totally to the attenuation in inflammatory cytokine/chemokine expression, IκBα expression, PMN recruitment and physiologically lower level of inflammation demonstrated in vivo in rats due to *B. thetaiotaomicron*.

5. PPARγ localised to the cytosol in the presence of *B. thetaiotaomicron*.

6. PPARγ and p65 are physically coupled when co-localised in the cytosol.

The present invention will now be illustrated further by reference to the following non-limiting, examples and to the figures in which:

Figure 1:
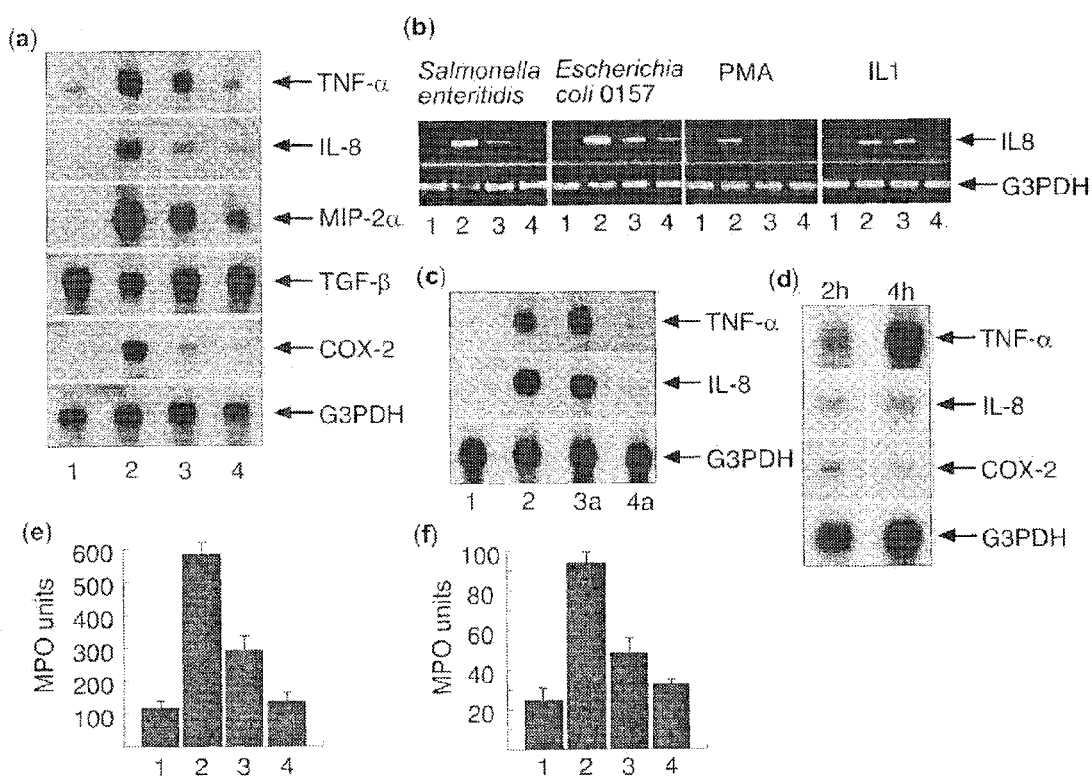
FIG. 1

(a) Northern blot hybridisation of cytokine mRNA using $^{32}$P-labelled probes specific for TNF-α, IL-8, MIP-2α, TGF-β, COX-2 and G3PDH of:
 1) Non-infected Caco-2 cells;
 2) Caco-2 cells with $10^8$ *S. enteritidis*;
 3) Caco-2 cells with $10^8$ *S. enteritidis* and $10^9$ *B. thetaiotaomicron*;
 4) Caco-2 cells with $10^9$ *B. thetaiotaomicron*.

(b) Semi-quantitative PCR of IL8 and G3PDH. Caco-2 cells incubated in medium alone (1); with either $10^8$ *S. enteritidis*, $10^8$ *E. coli* 0157 H7, PMA (300 ng/ml) or IL-1 α/β (20 ng/ml) as indicated (2); as described in (2) but in the presence of $10^9$ *B. thetaiotaomicron* (3); or with $10^9$ *B. thetaiotaomicron* (4).

(c) Northern blot hybridisation of mRNA using $^{32}$P-labelled probes specific for TNF-α, IL-8, MIP-2α, TGF-β, COX-2 and G3PDH of:
 1) Non-infected Caco-2 cells;
 2) Caco-2 cells with $10^8$ *S. enteritidis*;
 3) Caco-2 cells with $10^8$ *S. enteritidis* and $10^9$ *B. vulgatus*;
 4) Caco-2 cells with $10^9$ *B. vulgatus*.

(d) CaCo-2 cells were incubated with $10^8$ *S. enteritidis* and $10^9$ *B. thetaiotaomicron* for either 2 or 4 hours as indicated.

(e) Transepithelial migration of PMN cells though CaCo-2 monolayer as determined by MPO Assay of treatment groups (1) to (4) of (a) above.

(f) MPO Assay of ileal mucosa 6 days post treatment of rats challenged with (1) control; (2) $10^8$ *S. enteritidis*; (3) *B. thetaiotaomicron* then $10^8$ *S. enteritidis*; and (4) *B. thetaiotaomicron* alone. Data are means±SD (n=3).

FIG. 2

1) Non-infected Caco-2 cells;
2) Caco-2 cells incubated with $10^8$ *S. enteritidis*;
3) Caco-2 cells incubated with $10^8$ *S. enteritidis* and $10^9$ *B. thetaiotaomicron*;
4) Caco-2 cells incubated with $10^9$ *B. thetaiotaomicron* and probed with primary antibodies (A-D) anti-RelA; (E-H) anti-PPARγ; (I-L) anti-IκBα; and (M-P) anti pκβα. All Scale bars=25 µm. Inserts in O and P show details of punctate nuclear label.

FIG. 3

(A) Supershift EMSA performed on CaCo-2 nuclear extracts using a consensus $^{32}$P-labelled NF-κB binding sequence oligonucleotide and incubated with anti-RelA antibody on groups (1) to (4) as described above for FIG. 1A. Where indicated the *B. thetaiotaomicron* was heat inactivated at 70° C. for 15 minutes.

(B) Northern hybridisation of mRNA of experimental treatment groups were as described above (1-4), with blots probed with specific $^{32}$P-labelled IκBα and G3PDH probes.

(C) Western blot of nuclear extracts derived from Caco-2 cells. Treatment groups were as described above (1-4). Immunoblots were probed with specific antibodies to anti-p38 and anti-pp38 (New English Biolabs).

D) Superinduction of c-Fos and c-Jun were determined by Northern hybridisation on total RNA from Caco-2 cells. Treatments were, Caco-2 cells in the absence of cyclohexamide (-C) or as described above (1-4) but in the presence of 10 µg/ml cyclohexamide. The blots were hybridised with $^{32}$P-labelled probes specific for c-Fos, c-Jun and G3PDH.

E, F) Western blots of nuclear extracts derived from Caco-2 cells. Treatment groups were as described above (1-4). Specific antibodies to c-Fos (Santa Cruz), ATF-2 and pATF-2 (New England Biolabs) were used.

G) Immunoprecipitation (IP) using IκBα and pIκBα. Caco-2 cells following standard culture protocol, treatment groups (1-4). IP analysed by western blotting, NS indicates non-specific, B1 is a control with no cell extract.

FIG. 4

A) Northern hybridisation of mRNA from non-infected Caco-2 cells (1), Caco-2 cells following incubation with $10^8$ *S. enteritidis* (2), $10^8$ *S. enteritidis* and $10^9$ *B. thetaiotaomicron* (3), and $10^9$ *B. thetaiotaomicron* alone (4) analysed by specific $^{32}$P-labelled PPARγ and PPARα probes. Bacteria were applied for 2 hours.

B) Treatments (1) and (2) were as described above, or cells incubated with $10^8$ *S. enteritidis* in the presence of 30 µM 15PG-J$_2$ (3a) or 30 µM fenofibrate (3b) as indicated. Bacteria and drugs were applied for 2 hours. mRNA was analysed by Northern hybridisation with a $^{32}$P-labelled PPARγ specific probe.

C) mRNA from non-infected Caco-2 cells (1), Caco-2 cells following incubation with $10^8$ *S. enteritidis* (2), $10^8$ *S. enteritidis* in the presence of either 10, 20 or 30 µM 15PG-J$_2$ (3) (4) (5); or 30 µM 15PG-J$_2$ alone (6) was analysed by Northern hybridisation with $^{32}$P-labelled TNF-α, IL-8, COX-2 and G3PDH. Bacteria and drugs were applied for 2 hours.

D) mRNA from non-infected Caco-2 cells (1), Caco-2 cells following incubation with $10^8$ *S. enteritidis* (2), $10^8$ *S. enteritidis* in the presence of 10 or 30 µM ciglitazone (3) (4) was analysed by Northern hybridisation with $^{32}$P-labelled TNF-α, IL-8, COX-2 and G3PDH. Bacteria and drugs were applied for 2 hours.

E) mRNA from non-infected Caco-2 cells (1), Caco-2 cells following incubation with $10^8$ *S. enteritidis* (2), $10^8$ *S. enteritidis* and 30 µM fenofibrate (3) was analysed by Northern hybridisation with $^{32}$P-labelled TNF-α, IL-8, COX-2 and G3PDH. Bacteria and drugs were applied for 2 hours.

F) Nuclear and cytoplasmic extracts from non-infected Caco-2 cells (1), Caco-2 cells following incubation with $10^8$ *S. enteritidis* (2), $10^8$ *S. enteritidis* and $10^9$ *B. thetaiotaomicron* (3), and $10^9$ *B. thetaiotaomicron* alone (4) were analysed by Western blotting with anti-PPARγ (Santa Cruz). bacteria were applied for 2 hours. CaCo-2 cells prepared as nuclear and cytoplasmic fractions, or detergent soluble (D. soluble) or insoluble (D. insoluble) fractions.

G) Caco-2 cells co-cultured with $10^8$ *S. enteritidis* and $10^9$ *B. thetaiotaomicron* for 2 hours were lysed in PBS containing 1% Nonidet P40 solution and incubated overnight with a polyclonal anti-RelA Sepharose (Santa Cruz). Immuno-precipitates were resolved using SDS-PAGE. Western blots were developed using a monoclonal anti-RelA [NF-κB p65], anti-PPARγ antibodies and anti-HDAC3 (Santa Cruz).

H) Immunofluorescence microscopy of PARRγ (f-m, o) and RelA (n). Co-localization of PARRγ and RelA from plates n and o (p). Caco-2 cells were grown in medium alone (t,j); with $10^8$ S. enteritidis (g,k); with $10^8$ S. enteritidis and $10^9$ B. thetaiotaomicron (h,l, n-p); or with $10^9$ B. thetaiotaomicron (i,m). Treatments in the absence (t,i, n-p) or presence of 4 μM TSA (j-m). All scale bars=25 μm.

FIG. 5

Mutation of PPARγ interferes with B. thetaiotaomicron-mediated attenuation NF-κB and cytosolic sequestration of RelA.

A) Immuno-detection RelA. Caco-2 cells prepared following standard culture protocol, treatment groups (1-4). Immunoprecipitates prepared using anti-PPARγ sepharose conjugate.

B) In vitro translation showing RelA/PPARγ association

C) Caco-2 cells were transfected with PPARγ DN and a NF-κB luciferase reporter construct (DN), and compared with control cells transfected with NF-κB luciferase reporter alone (MOCK). Luciferase activity (expressed as % stimulation) was determined in non-infected Caco-2 cells (1), Caco-2 cells following incubation for a further six hours with $10^8$ S. enteritidis (2), and $10^8$ S. enteritidis in the presence of $10^9$ B. thetaiotaomicron (3).

D) Caco-2 cells were transfected with a constitutively expressing green fluoescent protein (GFP) construct (B, C) or PPARγ DN and GFP (D, E). All cells were incubated with $10^8$ S. enteritidis and $10^9$ B. thetaiotaomicron. Cells were then immuno-stained with anti-RelA (p65) specific antibody (Santa Cruz) and examined by LSCM. (B) and (D) dual channel capture showing combined GFP (green) and RelA (red) images. (B) and (D) same areas as (B) and (D) respectively, with single channel capture showing only RelA. Scale bars=25 μM.

E) Caco-2 cells were transfected with RelA chimeric construct with carboxyl-terminus of yellow fluorescent protein (YFP) and either PPARγ (d-f) or PPARγ DN (g-i), both as chimeras constructs with carboxyl-terminus of cyan fluorescent protein (CFP). Two days post transfection, cells were incubated with $10^8$ S. enteritidis and $10^9$ B. thetaiotaomicron. CFP fluorescence (d,g) and YFP fluorescence (e,h). Colocalization of CFP-PPARγ and YFP-RelA from plates d and e (f), and CFP-PPARγ (DN) and YFP-RelA from plates g and h (i). All Scale bars=25 μm. (j,k). Hela cells were transfected with CFP-PPARγ and 2 days post transfection were incubated with $10^8$ S. enteritidis and $10^9$ B. thetaiotaomicron. Hela cells fixed, permeabilized and immuno-stained for SC35. CFP-PPARγ (j) indirect immunofluorescence of SC35 (k). Scale bars=10 μm.

FIG. 6

Figure 6:
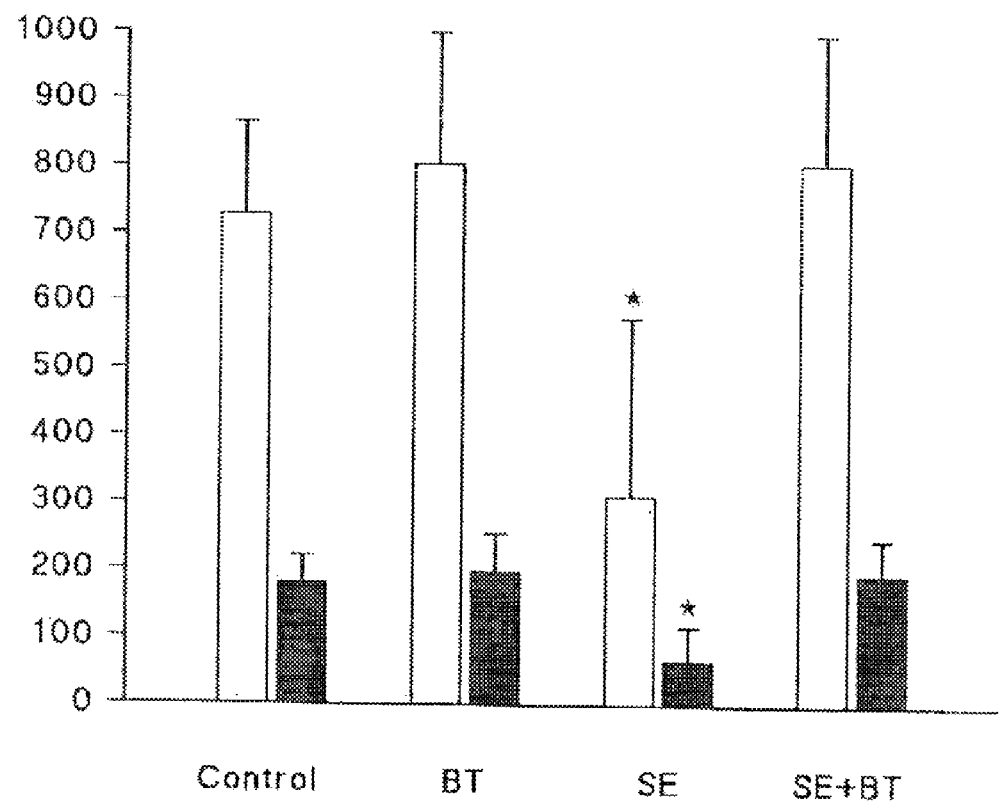

FIG. 6 shows skeletal muscle (□, wet weight and ■, dry weight) accretion (mg/rat d$^{-1}$) by control rats or rats orally treated with Bacterioides thetaiotaomicron (BT), Salmonella enterica var. enteritidis (SE) or S. enteritidis plus B. thetaiotaomicron (SE+BT). * shows significant difference to control, BT or SE+BT for dry weight and wet weight respectively ($p \leq 0.05$). Gastrocnemius muscle is taken as representative of skeletal muscle and total skeletal muscle in young Hooded-Lister rats as approximately 47 times the weight of the gastrocnemius muscle (Bardocz et al, 1996). Initial weight of gastrocnemius muscles 804±10 mg wet weight [194±7 mg dry weight] per 100 g initial fresh body weight.

FIG. 7

Figure 7:
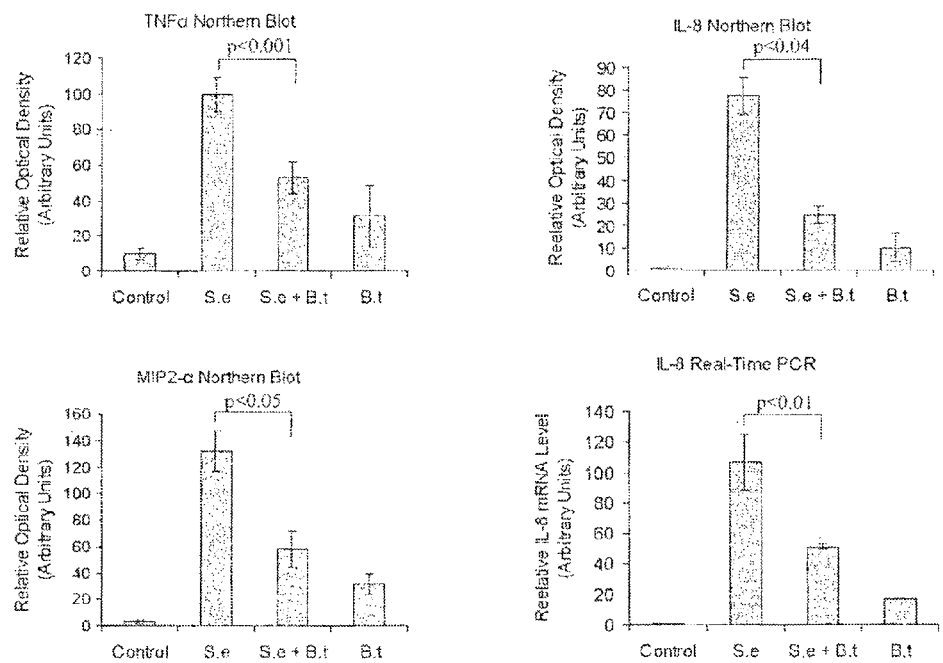

FIG. 7 shows quantitative data (Northern blot or real time PCR) illustrating effects on chemokine/cytokine mRNA expression. S.e.=S. enteritidis. B.t.=B. thetaiotaomicron.

FIG. 8

Figure 8:
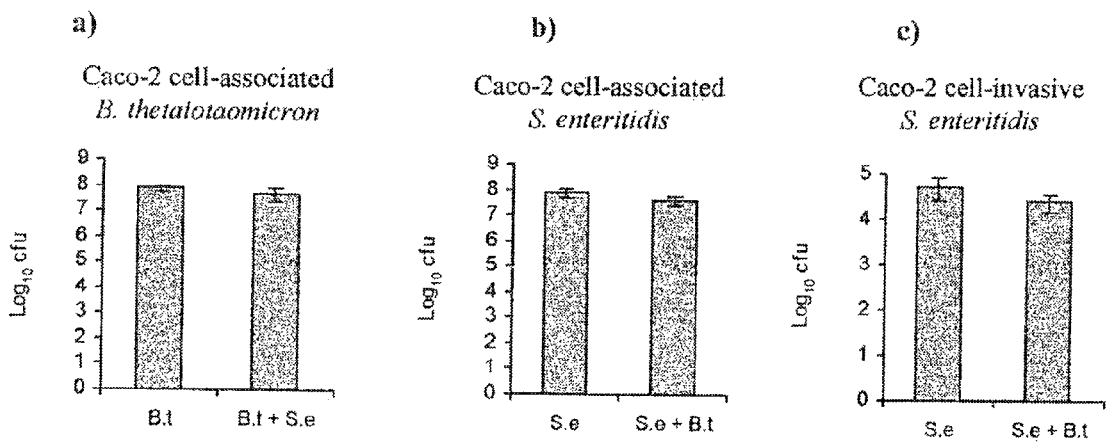

FIG. 8 shows bacterial counts following a 2 hour incubation with Caco-2 cell monolayer.

a) Caco-2 cell associated B.t (those remaining after washing cell layer) in the presence and absence of B.t.

b) Cell associated S.e in the presence and absence of B.t.

c) invaded Salmonella (those remaining after cell washing and treatment with gentamycin (100 μg/ml for 4 hours) in the presence and absence of B.t. n=6 +/− standard deviation.

FIG. 9

Figure 9A:
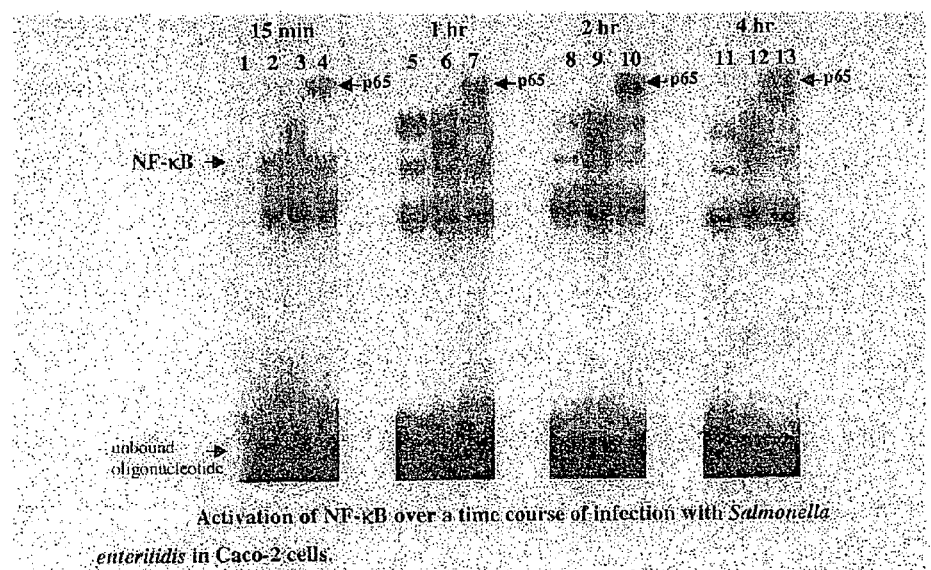

FIG. 9A: Shows NF-κB activation in Caco-2 cells in response to S. enteritidis using EMSA.

FIG. 9B: Analysis of cytokine response by Northern hybridisation.

a) mRNA from Caco-2 cells following 2 hour exposure to $10^8$ and $10^{10}$ cfu of S.e was analysed for induction of proinflammatory cyokines and normalised against G3PDH.

b) mRNA from Caco-2 cells following exposure to $10^9$ S.e for variable time periods was analysed for induction of proinflammatory cytokines and normalised against G3PDH. Data for up to 2 and 4 hours (FIG. 9D) is also shown.

c) mRNA from Caco-2 cells following 2 hour exposure to $10^7$ to $10^{10}$ B.t. was analysed for pro-inflammatory cytokines and normalised against G3PDH.

d) mRNA from Caco-2 cells analysed for inflammatory cytokine expression (COX-2 and IL-8), illustrating the suppressive effects of B.t. at 2 hours and 4 hours.

Figure 9C:
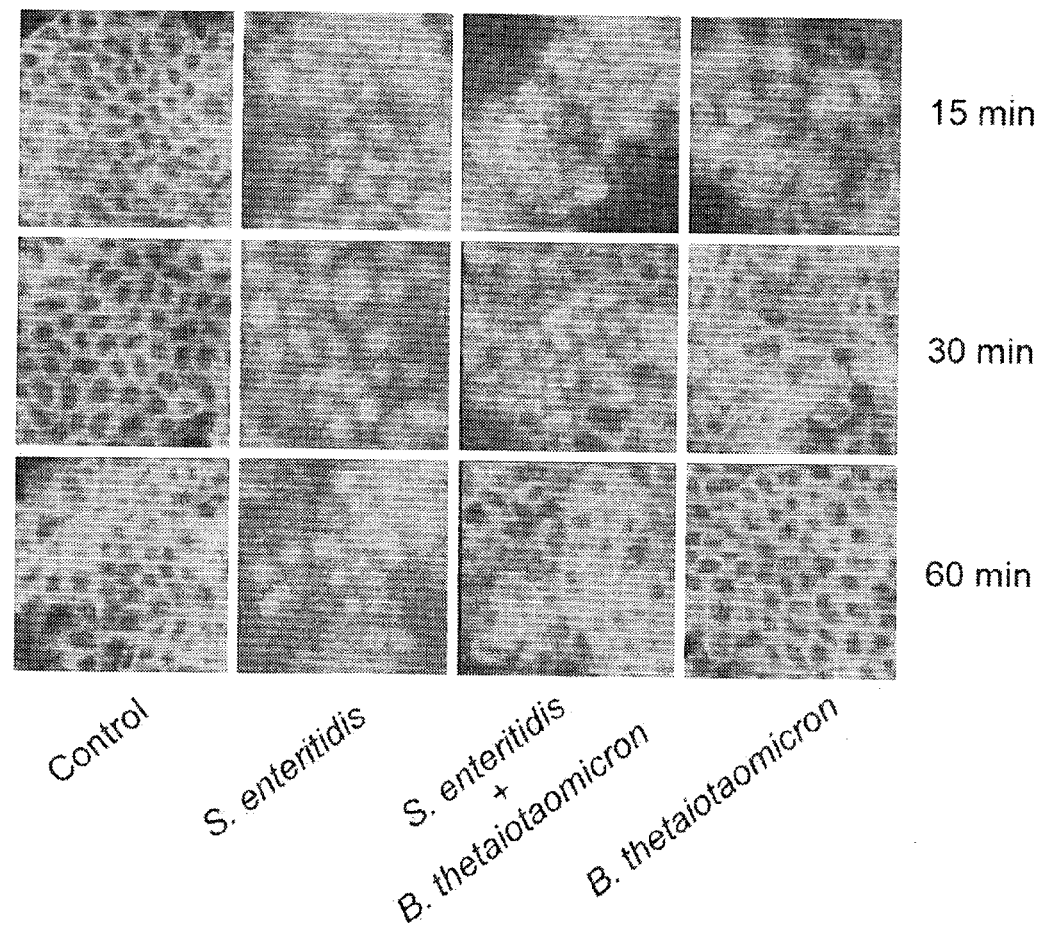

FIG. 9C: Time course of Rel (p65) activation following exposure of Caco-2 cells to S. enteritidis and B. thetaiotaomicron using immunocytochemical detection. Caco-2 cells exposed to S.e.+/− B.t. for 2 hours were fixed in 4% paraformaldehyde, permeabilised with Triton X-100 and immunolabelled with anti-p65 (RelA) (Santa Cruz). Secondary detection was with Alexa Fluor 488 anti-rabbit IgG (Molecular Probes). Images were digitally captured using a Zeiss Axiocam on an Axiovert 2000 Microscope.

Figure 9D:
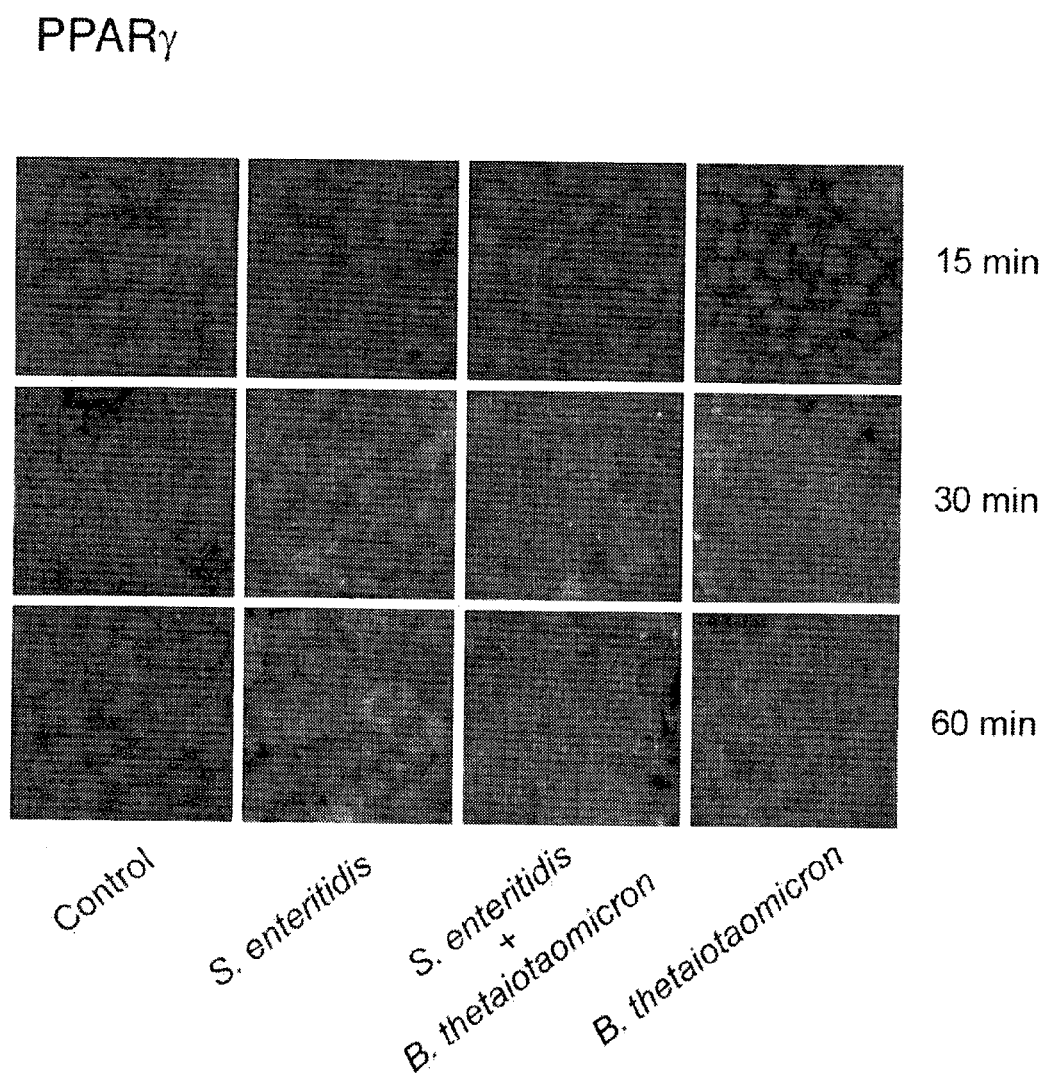
Figure 9E:
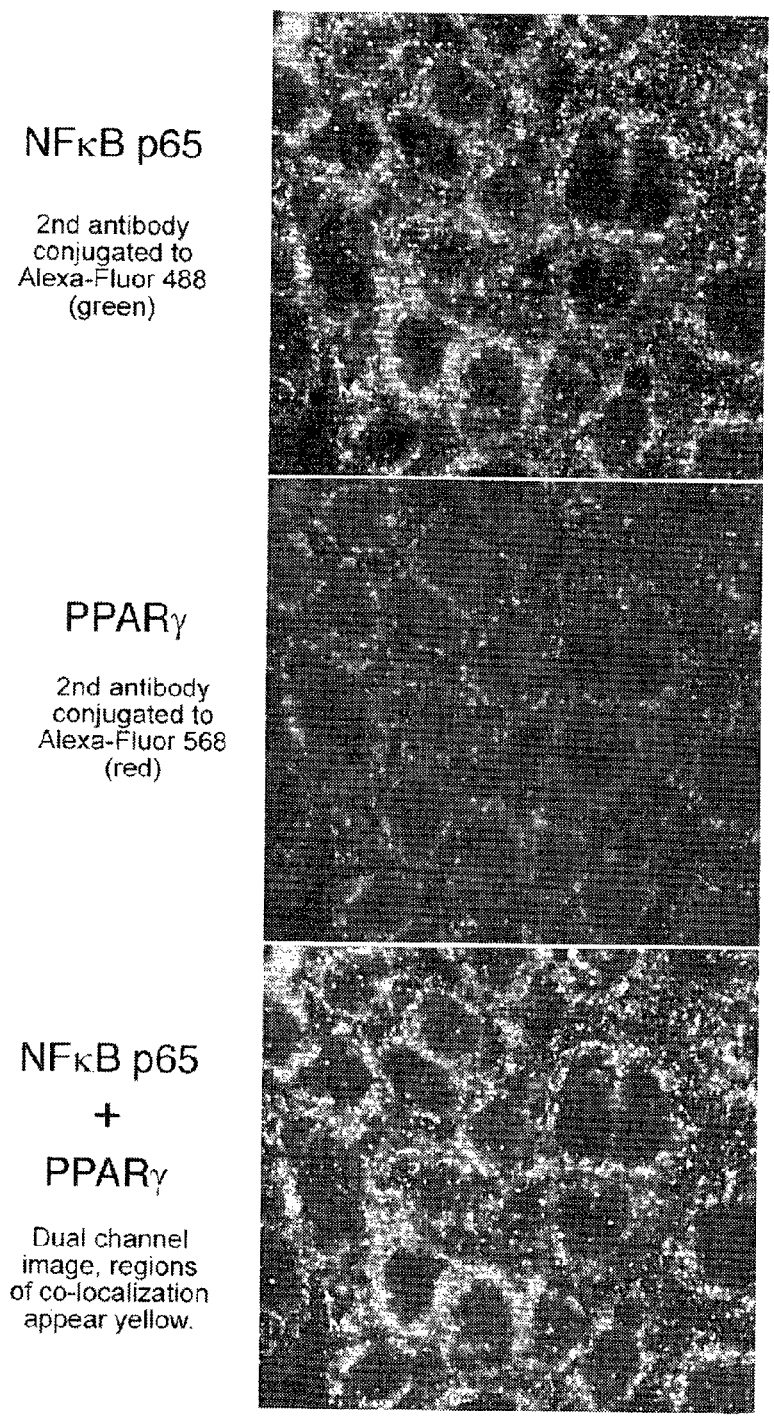

FIG. 9D: Time course of PPARγ effects following exposure of Caco-2 cells to S. enteritidis and B. thetaiotaomicron using immunocytochemical detection.

Caco-2 cells exposed to S.e.+/− B.t. for 2 hours were fixed in 4% paraformaldehyde, permeablised with Triton X-100 and immunolabelled with anti-PPARγ (Santa Cruz). Secondary detection was with Alexa Fluor 568 anti-goat IgG (Molecular probes). Images were digitally captured using a Zeiss Axiocam on an Axiovert 200 Microscope.

FIG. 9E

Shows co-labelling of NF-κB p65 and PPARγ in Caco-2 cells following 2 hour exposure to B. thetaiotaomicron and S. enteritidis.

FIG. 10

Skeletal muscle (Gastrocnemius muscle) (□, wet weight and ■, dry weight) accretion (mg/rat d$^{-1}$) by control rats or rats orally treated with B. thetaiotaomicron [B.t], Salmonella enterica var. enteritidis [S. e] or S.e+B.t n=6, +/−Standard Error.

FIG. 11

Shows p65 immunoprecipitates, separated using SDS-PAGE, electroblotted and immunostained with acetylated lysine monoclonal antibody.

DETAILED DESCRIPTION OF THE INVENTION

Example 1

Inflammatory Responses of Caco-2 Cells Exposed to S. enteritidis in the Presence and Absence of B. thetaiotaomicron and B. vulgatus.

The evidence for bacterial regulation of host inflammatory response was derived from studies investigating inflammatory gene expression following short-term exposure of intestinal Caco-2 cells to *Salmonella enteritidis* co-cultured in the presence and absence of *Bacteroides thetaiotaomicron*. Using cDNA macro-array technology (CLONTECH Atlas human cytokine/receptor array system) we identified several genes including TNF-α, IL-8, MIP-2α and COX-2, whose induction following *S. enteritidis* exposure was attenuated by the presence of *B. thetaiotaomicron*. These results were confirmed using Northern hybridization and real-time PCR (FIG. 1a, f). We also investigated the anti-inflammatory activity of *B. thetaiotaomicron* against other inflammatory mediators including IL-1α, IL1-β, TNF-α, PMA, LPS and enterohaemorrhagic *E. coli* O157 H7 (FIG. 1F). Of those ligands that induced IL-8 expression in Caco-2 cells, only the PMA, *S. enteritidis* and *E. coli* O157 H7 effects were attenuated by *B. thetaiotaomicron*.

In setting the experimental conditions for these studies, many optimisation experiments (including time course, bacterial dose/growth phase, Caco-2 cell passage/confluence studies) were undertaken. Importantly we established that the growth, attachment and invasion of bacteria were unaffected by culture/co-culture conditions, thereby ruling out the possibility that the data could be attributed to differential attachment/invasion (see FIG. 8).

Inflammatory gene expression was determined in non-infected Caco-2 cells (1), cells incubated with $10^8$ *S. enteritidis* alone (2), cells incubated with $10^8$ *S. enteritidis* and $10^9$ *B. thetaiotaomicron* (3) or cells incubated with $10^9$ *B. thetaiotaomicron* alone (4). Bacteria were applied for 2 hours. Cells were washed and harvested for mRNA isolation and 5 µg of mRNA was analysed by Northern hybridisation with $^{32}$P-labelled probes specific for TNF-α, IL-8, MIP-2α, TGF-β, COX-2 and G3PDH.

Some of the results describing the effects of *B. thetaiotaomicron* are consistent with the recent molecular analysis reporting by Hooper et al, 2001. Our results were confirmed using Northern hybridisation and real-time PCR. Levels of TNF-α, IL-8, MIP-2α and COX-2 were significantly increased in response to *S. enteritidis* challenge (FIG. 1a). In the presence of *B. thetaiotaomicron* however, the level of expression of these genes were all attenuated with the exception of TGF-β, which was decreased by *S. enteritidis* yet maintained at control values by the presence of *B. thetaiotaomicron*. The viability and growth rates of both bacteria and the numbers of *S. enteritidis* adhering and invading epithelial cells did not differ between the treatments and were unaffected by the culture procedure.

The quantitative data shown in FIG. 7 confirms these results and was obtained using mRNA purified from Caco-2 cells following a 2 hour incubation with vehicle (control), $5×10^8$ *Salmonella enteritidis* (S.e), $5×10^8$ S.e and $1.5×10^9$ *B. thetaiotaomicron* (B.t) or B.t alone. Northern blots were quantified by densitometry and normalised to G3PDH levels. Real time PCR was performed using ABI Taqman and normalised to 18S rRNA levels. n=4 +/− standard deviation.

To investigate whether the attenuation of inflammatory cytokine expression was specific to *B. thetaiotaomicron* a related aerotolerant strain, *B. vulgatus*, was also studied.

Treatments were as described above for (1) and (2), cells incubated with $10^8$ *S. enteritidis* and $10^9$ *B. vulgatus* (3a) or cells incubated with $10^9$ *B. vulgatus* alone (4a). Bacteria were applied for 2 hours.

*B. vulgatus* was negative for the biological activity (see FIG. 1b).

In the results obtained the small induction of inflammatory gene expression triggered by both of the commensal strains, which may be related to the fact that late log phase bacteria were tested; was noteworthy. The application of early log phase bacteria devoid of bacterial cell debris, may completely abrogate this response. A further experiment was therefore conducted in which Caco-2 cells were incubated with $10^8$ *S. enteritidis* and $10^9$ *B. thetaiotaomicron* for either 2 or 4 hours. The inhibitory effect of *B. thetaiotaomicron* on IL-8 expression was sustained for prolonged periods (FIG. 1d), which contrasted with TNF-α, suggesting that the mechanisms regulating the expression of these genes are differentially influenced by *B. thetaiotaomicron*.

The physiological relevance of the data showing the suppression of inflammatory cytokines by *B. thetaiotaomicron* was verified using both a functional in vitro model of PMN recruitment and an in vivo *S. enteritidis* rat infection model. PMN recruitment in vitro and in vivo was monitored using myeloperoxidase (MPO) activity.

Caco-2 cells were seeded onto inverted Transwells (Corning) and various combinations of bacteria applied to the apical surfaces of the cells. Freshly isolated human PMNs were applied to the basolateral compartment and their transepithelial migration determined by MPO assay (Neish et al, 2000). Treatment groups (1-4) were as described above. Cells were incubated for 2 hours and then bacteria were removed and fresh media applied. Cells were incubated for a further 2 hours and then washed in HBSS. Both cells, and media derived from the apical compartment, were solubilised in a 1% Triton C-100 and MPO determined.

The results derived from the in vitro model of polymorphonuclear leukocyte (PMN) recruitment assay confirmed the anti-inflammatory activity of B. thetaiotaomicron (FIG. 1e).

It is noteworthy that *S. enteritidis* infection of the rat intestine is mainly in the ileum, the natural habitat for *B. thetaiotaomicron*.

Newly weaned (21 d) minimal flora rats (fed on normal laboratory diets) were split into 2 groups and one group additionally fed with anaerobically prepared jelly (0.5 g/d) containing $10^8$ cfu of *B. thetaiotaomicron* for 19 days. Half of the rats in each group were then orally challenged with $10^8$ *S. enteritidis*. The severity of the inflammatory response in all animals was assessed by determining MPO levels in ileal mucosa at 6 days post *S. enteritidis* infection. Treatments were, no *B. thetaiotaomicron* and no *S. enteritidis* (1), no *B. thetaiotaomicron* then $10^8$ *S. enteritidis* (2), *B. thetaiotaomicron* then $10^8$ *S. enteritidis* (3), and *B. thetaiotaomicron* alone (4). Experiments were undertaken at least 3 times with similar results.

The level of MPO in the ileal mucosa of rats challenged with *S. enteritidis* increased ($P<0.005$), but was significantly attenuated by prior oral inoculation and stabilisation of *B. thetaiotaomicron* within the flora ($P<0.001$) (FIG. 1f). Furthermore, from the PMN recruitment experiments we found that *S. enteritidis* induced 400 pg/ml IL-8 protein in culture supernatants over 4 h whereas when co-cultured in the presence of *B. thetaiotaomicron* the concentration was significantly lower at 230 pg/ml. Colonisation by *B. thetaiotaomicron* was confirmed by specific primer amplification of intestinal tissues. As IL-8 and MIP-2α are essential chemokines for PMN transepithelial migration (McCormick et al, 1993; Hang et al, 1999), the effects of *B. thetaiotaomicron* are therefore due to decreased IL-8 and MIP-2α transcription, which then impacts on the translation and secretion of active protein. Consistent with Neish et al, 2000 we have demonstrated, using a novel model system, that non-pathogenic bacteria can exert immune suppressive effects by subverting host systems that regulate gene expression. Importantly, we have also provided in vivo validation of our findings.

Figure 10:
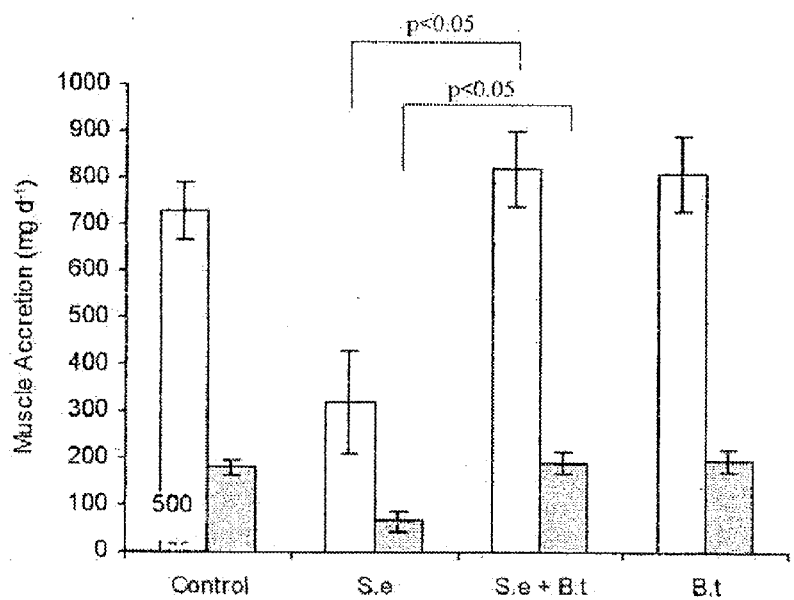

In addition to MPO data discussed above FIG. 10 illustrates further evidence of the protective effects of *B. thetaiotaomicron* on muscle biology during the inflammatory response induced by *S. enteritidis*.

Example 2

*B. thetaiotaomicron* Attenuates Inflammation by Altering the Cellular Distribution and Activation State of NF-κB and PPARγ Proteins and Involves Targeted Disruption of the NF-κB Signal Transduction Pathway.

The NF-κB family of transcription factors plays a central role in regulating inflammatory responses.

These proteins share a highly conserved $NH_2$-terminal sequence referred to as the Rel homology domain, which is required for their subunit dimerisation, DNA binding and interaction with the inhibitory IκB proteins. Signals that induce NF-κB lead to phosphorylation, of the inhibitory IκB proteins (IκBα at Ser-32 and Ser-36) which are then targeted for ubiquitination and proteosome-meditated degradation. Rel proteins, including RelA (p65), are thereby released to translocate to the nucleus and bind DNA.

Non-infected Caco-2 cells (1) were incubated with $10^8$ *S. enteritidis* alone (2), $10^8$ *S. enteritidis* and $10^9$ *B. thetaiotaomicron* (3), and $10^9$ *B. thetaiotaomicron* alone (4) for 2 hours. Cells were fixed in 4% paraformaldehyde for 30 minutes at room temperature, permeabilised with 0.2% Triton-X 1000 at 4° C. and examined by indirect immunofluorescence microscopy. Primary antibodies (Santa Cruz) (A-D) anti-RelA [NF-κB p65], (E-H) anti-PPARγ, (I-L) anti-IκBα and (M-P) anti-pκBα. Secondary antibodies: Alexa Fluor species-specific anti-IgG (Molecular Probes).

Figure 2:
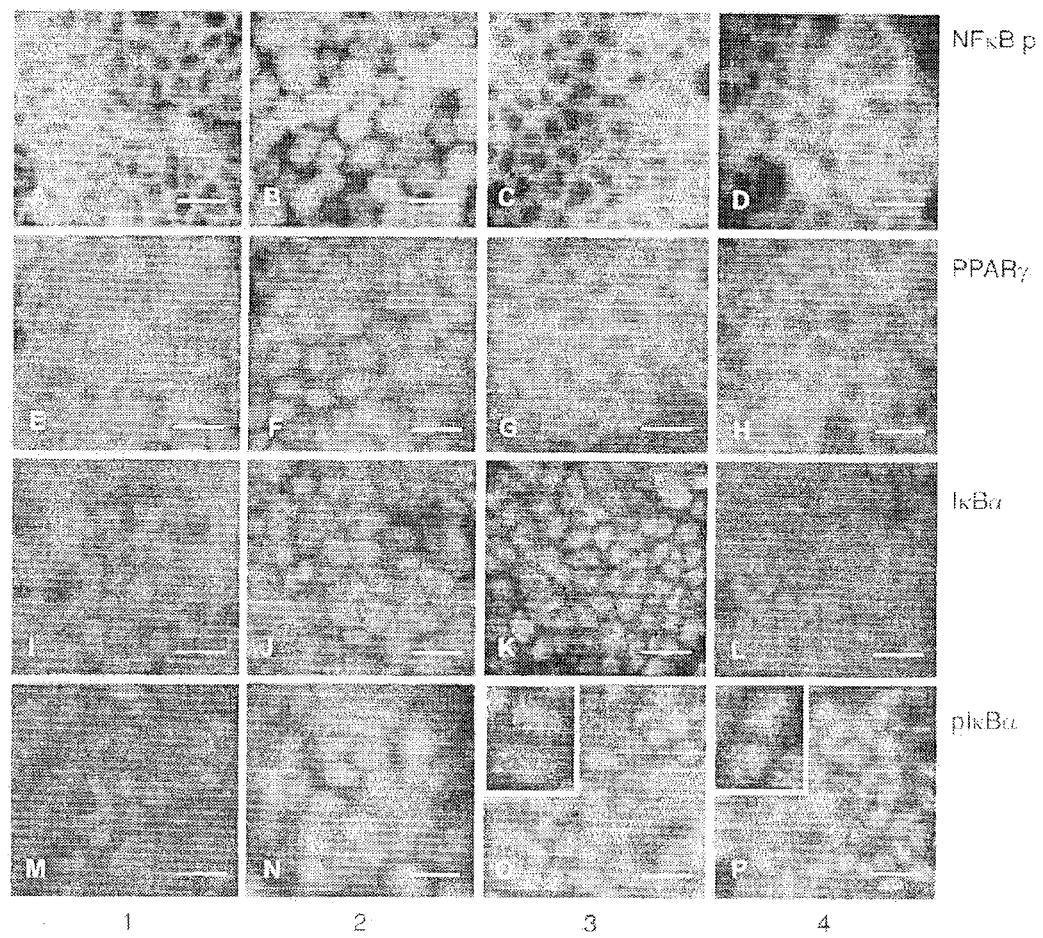

We found that exposure of Caco-2 cells to *S. enteritidis* triggered a cascade of events leading to enhanced translocation of RelA to the nucleus (FIG. 2B).

Significantly, *B. thetaiotaomicron* was found to abolish the translocation of RelA to the nucleus with virtually all RelA localised to the cytosol following 2 hours of exposure to this bacterium (FIG. 2C, D).

Phosphorylation of IκBα and, importantly, its degradation was observed following exposure to *S. enteritidis* in the presence and absence of *B. thetaiotaomicron* (FIG. 2G). Following 2 h exposure, both the level of IκBα mRNA (FIG. 3B) and protein (FIG. 2J, K) were enhanced, particularly in cells exposed to *S. enteritidis* alone and *S. enteritidis/B. thetaiotaomicron*, indicating the presence of transcriptionally active NF-κB (Cheng et al. 1994; Chiao et al. 1994).

Viable *B. thetaiotaomicron* Selectively Interferes with the Transcriptional Activity of NF-κB Proteins but does not Influence the Synthesis or Phosphorylation of AP-1 Proteins.

Supershift EMSA performed on nuclear extracts, incubated with RelA [NF-κB p65] specific antibody (Santa Cruz), from non-infected Caco-2 cells (1) following incubation with $10^8$ *S. enteritidis* (2), $10^8$ *S. enteritidis* and $10^9$ *B. thetaiotaomicron* (3), and $10^9$ *B. thetaiotaomicron* alone (4) for 2 hours. Where indicated *B. thetaiotaomicron* was heat inactivated at 70° C. for 15 minutes prior to its addition to the Caco-2 cells.

Using electrophoretic mobility shift assays (EMSA) we confirmed that RelA was the major subunit activated by *S. enteritidis* (FIG. 3A), although a lower level activation of p52 was also apparent (data not shown). We then hypothesised that *B. thetaiotaomicron* attenuated the production of immune response mediators, triggered by Salmonella, by disrupting the NF-κB signal transduction pathway.

A similar experiment is illustrated in FIG. 9A which demonstrates EMSA supershifts showing peak activation of p65 at 2 hours following exposure to *S. enteritidis* in Caco-2 cells. Lane 1, no protein, lanes 2, 5, 8, 11 nuclear extracts from control cells; lanes 3, 6, 9, 12 nuclear extracts from cells infected with S.e.; lanes 4, 7, 10, 13 nuclear extracts for cells infected with S.e. and supershifted with p65 (RelA) antibody.

Figure 3:
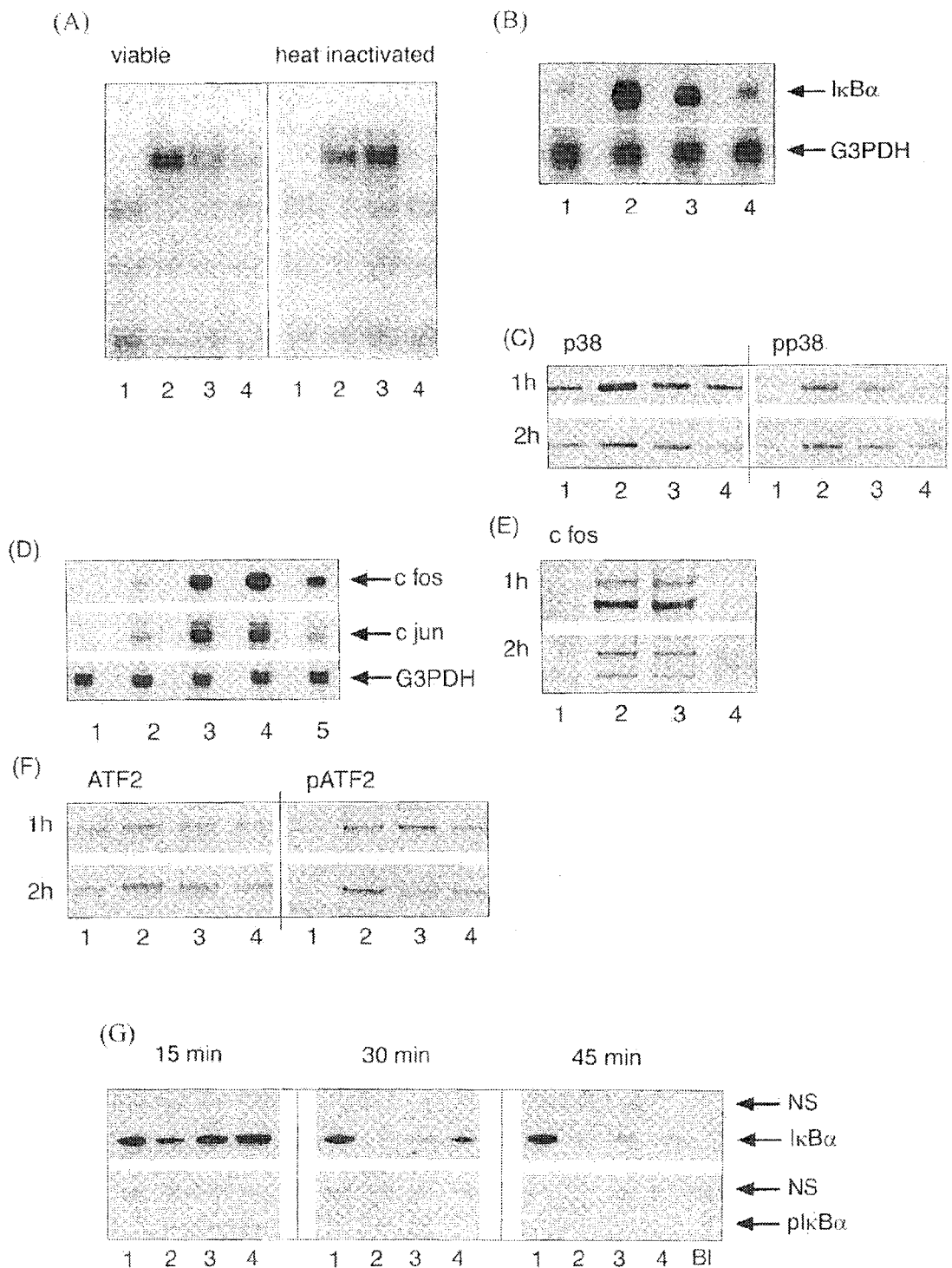

We also showed that viable but not heat-inactivated *B. thetaiotaomicron* inhibited the RelA response (FIG. 3A). Similarly, neither bacterial culture supernatant nor conditioned culture media (media from Caco-2 cells exposed to *B. thetaiotaomicron*) possessed biological activity (data not shown). This suggests that epithelial cell contact is essential for the anti-inflammatory activity of *B. thetaiotaomicron*. Within 20 minutes of exposure to *S. enteritidis*, in the presence and absence of *B. thetaiotaomicron*, IκBα phosphorylation and degradation was observed (data not shown).

Furthermore, the viability, growth, attachment and invasion of the bacterial strains studied were unaffected by culture treatments (data not shown) and hence the observed effects cannot be ascribed to differences in receptor recognition and activation.

Using the same experimental groups (1-4) as described above, bacteria were applied for 2 hours before mRNA was analysed by Northern hybridisation and blots probed with specific $^{32}$P-labelled IκBα and G3PDH probes. Both the levels of IκBα mRNA (FIG. 3B) and IκBα protein (FIG. 2J, K) were enhanced. This increase could be ascribed to the transcriptional activity of RelA which induces neo-synthesis of IκBα protein (Cheng et al, 1994). IκBα then enters the nucleus and associates with RelA removing it from DNA promoter sites (Arenzana-Seisdedos et al, 1995). Interestingly, PPARα-mediated stimulation of IκBα synthesis has also been reported (Delerive et al, 2000). To further investigate if a transient RelA translocation does occur in *B. thetaiotaomicron* treated cells experiments were undertaken using leptomycin B (LMB), a specific inhibitor of CRM-1-dependent nuclear export. The rationale was that the cytoplasmic location of Rel proteins, including p65, is maintained by CRM-1-dependent export of RelA/IκBα complexes out of the nucleus (Huang et al, 2000; Tam et al, 2000). We found that LMB caused an accumulation of RelA in nuclei of cells co-cultured with both *S. enteritidis* and *B. thetaiotaomicron* (results not shown) indicating that, independent of the presence of *B. thetaiotaomicron*, transient RelA translocation to the nucleus does occur. This result is consistent with the phosphorylation and ubiquitination of the cytosolic IκBα/RelA complex and the activation of IκBα gene expression following initial exposure of intestinal cells to bacteria.

Example 3

Figure 4:
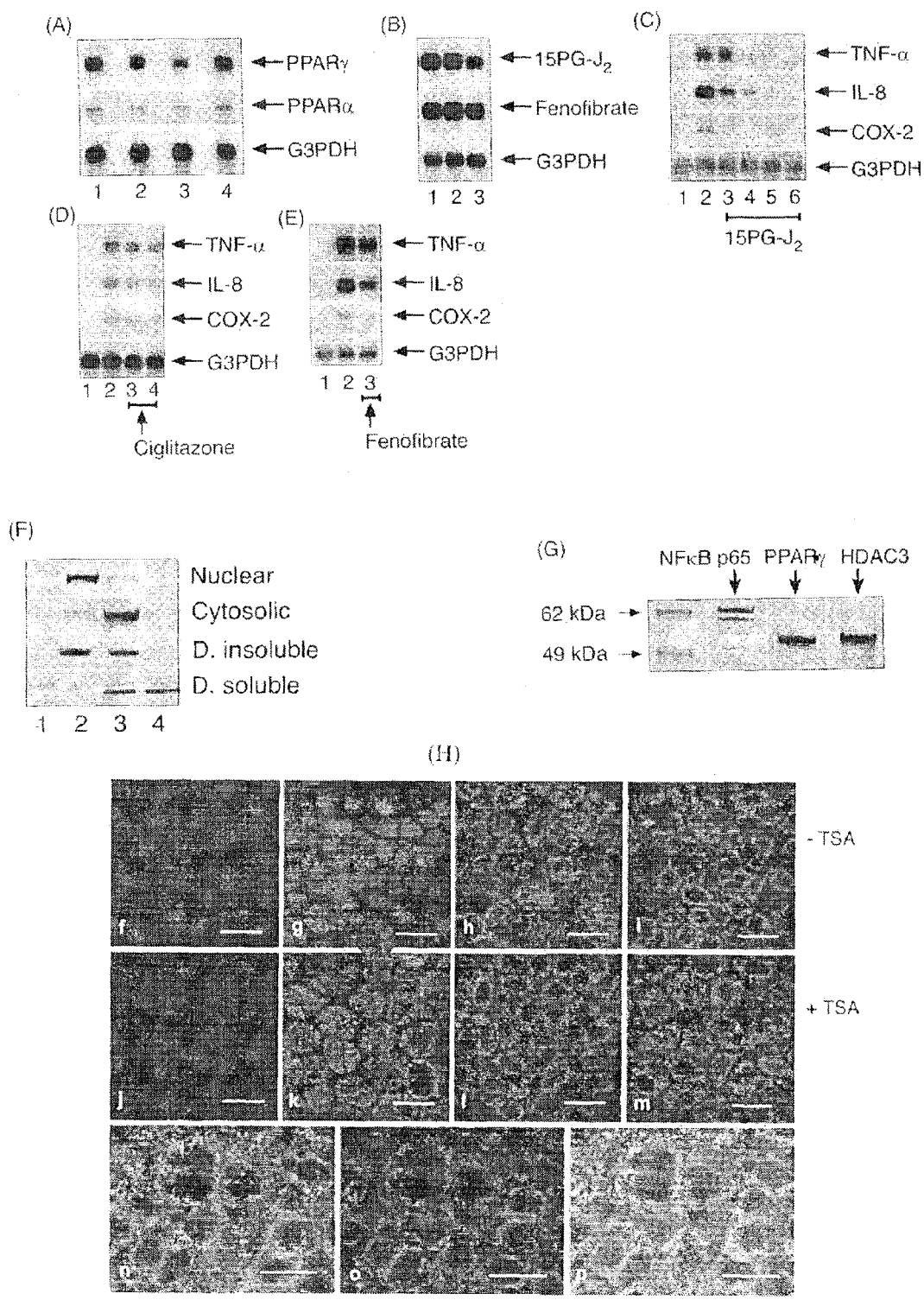
Figure 11:
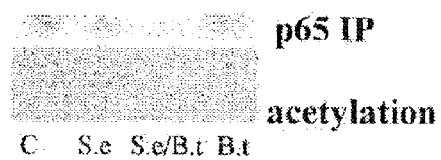

*B. thetaiotaomicron* Induces Nucleocytoplasmic Shuttling of PPARγ and Sequesters RelA A recent report of immune-suppression by non-pathogenic bacteria attributed the mechanism to inhibition of both ubiquitination and degradation of IκBα (Neish et al, 2000), which clearly does not apply to our model system. The predominant cytosolic location of NF-κB complexes in cells co-cultured with both *S. enteritidis* and *B. thetaiotaomicron* could then be explained by a greater efficiency of the IκBα-mediated nuclear export over nuclear localisation. The levels of IκBα protein are moderately higher in the nuclei of cells treated with both *S. enteritidis* and *B. thetaiotaomicron* than *S. enteritidis* alone, which could potentially accelerate the deactivation of NF-κB and contribute to the overall anti-inflammatory properties of *B. thetaiotaomicron*. However, a more likely explanation is the differential deacetylation of RelA. It has recently been reported that the duration of nuclear RelA activation is determined by reversible acetylation (Chen et al, 2001). The acetylated form of RelA has a low affinity for IκBα whereas the deacetylation of RelA by histone deacetylase 3 (HDAC3) promotes the binding to IκBα and the CRM-1-mediated nuclear export of RelA. We showed that *B. thetaiotaomicron* promoted HDAC3 association with RelA (FIG. 4G). Experiments using trichostatin A (TSA), a specific inhibitor of histone deacetylases, were undertaken. Results showed that inhibition of HDACs, in response to TSA treatment (800 nM for 4 hours), resulting in partial p65 accumulation but importantly an accelerated exit of PPARγ to cytosol in cells treated with *S. enteritidis* alone. The data presented supports the role of acetylation/deacretylation as an important mechanism facilitating nuclear export of p65 and PPARγ in *B thetaiotaomicron* treated cells (see FIG. 11).

Furthermore, both RelA and peroxisome proliferator-activated receptor gamma (PPARγ) proteins appeared to co-localise within the same cellular compartment (FIG. 2C, G) and we also hypothesised that an important mechanism limiting further RelA nuclear translocation in *B. thetaiotaomicron* treated cells involves cytosolic sequestration of RelA by PPARγ. The supporting experimental evidence is presented below.

AP-1 complexes play an important role in the regulation of inflammatory gene expression and are rapidly activated by a variety of extracellular stimuli including growth factors, cytokines and bacteria (Meyer-ter-Vehn et al, 2000). We investigated whether the inhibitory effects of *B. thetaiotaomicron*, extended to this signalling pathway. AP-1 activity is regulated by two main mechanisms, involving enhanced expression and phosphorylation of AP-1 subunits consisting of homo- and hetero-dimers of the protooncogene families Fos (c-Fos, FosB, Fra-1 and Fra-2), Jun (JunB, c-Jun and JunD) and ATF (ATF2, ATF3/LRF2 and B-ATF), all members of the leucine zipper family of DNA binding proteins. These proteins are mainly controlled by three related kinases, collectively called mitogen-activated protein (MAP) kinases. We investigated whether the level of protein phosphorylation of p42 and p44 (extracellular signal-regulated kinase; ERK) kinases, the c-Jun N-terminal kinases (JNK)/stress-activated protein (SAP) kinases and the p38 kinases were altered in response to *S. enteritidis* and *B. thetaiotaomicron*. We found that *S. enteritidis* activated p38 MAP kinase (FIG. 3C) but not ERK or JNK during the time period studied (results not shown). This finding is consistent with the fact that p38 is rapidly activated by inflammatory stimuli (Raingeaud et al, 1996), whereas the activation of JNK can occur at a later time point (Kujime et al, 2000). Activation of p38 leads to phosphorylation of elk-1, which in conjunction with serum response factor, binds to the serum response element in the c-fos promoter, to increase c-fos transcription and translation, as shown by changes in the gene and protein levels (FIG. 3D, E). We showed that the p38 phosphorylation induced by Salmonella was not modified by co-incubation with *B. thetaiotaomicron*. Message and protein levels were both increased in response to *S. enteritidis* and *B. thetaiotaomicron* and the effects on c-fos gene expression appeared to be additive. De Novo c-Fox synthesis leads to the formation of Jun-Fos hetero-dimers, which have a 10-fold higher DNA binding affinity, resulting in increased AP-1 activity (Musti et al, 1997; Smeal et al, 1991). ATF-2 is also a target of the p38 MAP kinase and JNK signal transduction pathways. The transcription factor ATF-2 is phosphorylated by p38 MAP kinase on Thr-69 and Thr-71. JNK however, phosphorylates and activates both ATF-2 and c-Jun. ATF-2 and c-Jun are therefore, differentially regulated by p38 and JNK signal transduction pathways (Raingeaud et al, 1996). In our study neither an increase in c-Jun protein level nor its phosphorylation state was observed in response to either bacterial strain, indicating that the phosphorylation of ATF-2 in response to *S. enteritidis* (FIG. 3F) is likely to be induced by p38 MAP kinase and not JNK. These data are consistent with the direct effect of *S. enteritidis* on the p38 MAP kinase activity. It is likely that ATF-2 activation triggers the formation of c-Jun/ATF-2 hetero-dimers that then stimulate c-jun gene transcription in response to Salmonella (FIG. 3D). The anti-inflammatory effects of *B. thetaiotaomicron* appear to target the NF-κB pathway selectively and this may explain why genes such as IL-8 that have an absolute requirement for NF-κB (Mukaida et al, 1994; Elliott et al, 2001) are particularly sensitive to inhibition by *B. thetaiotaomicron*.

Example 4

To further investigate the mechanism of immune suppression by non-pathogenic bacteria we initially studied the anti-inflammatory cytokines, IL-10 and TGF-β. IL-10 gene expression was not affected by treatment with *B. thetaiotaomicron* (data not shown) although this does not preclude the possibility that constitutive protein may be involved. There was some suggestion from the data that the contra-inflammatory cytokine TGF-β may be involved. However, if this cytokine is acting to down-regulate inflammatory responses, it is more likely to be involved in the longer-term anti-inflammatory effects, as de novo cytokine synthesis would not have been significant over the time course of these acute studies.

Figure 5:
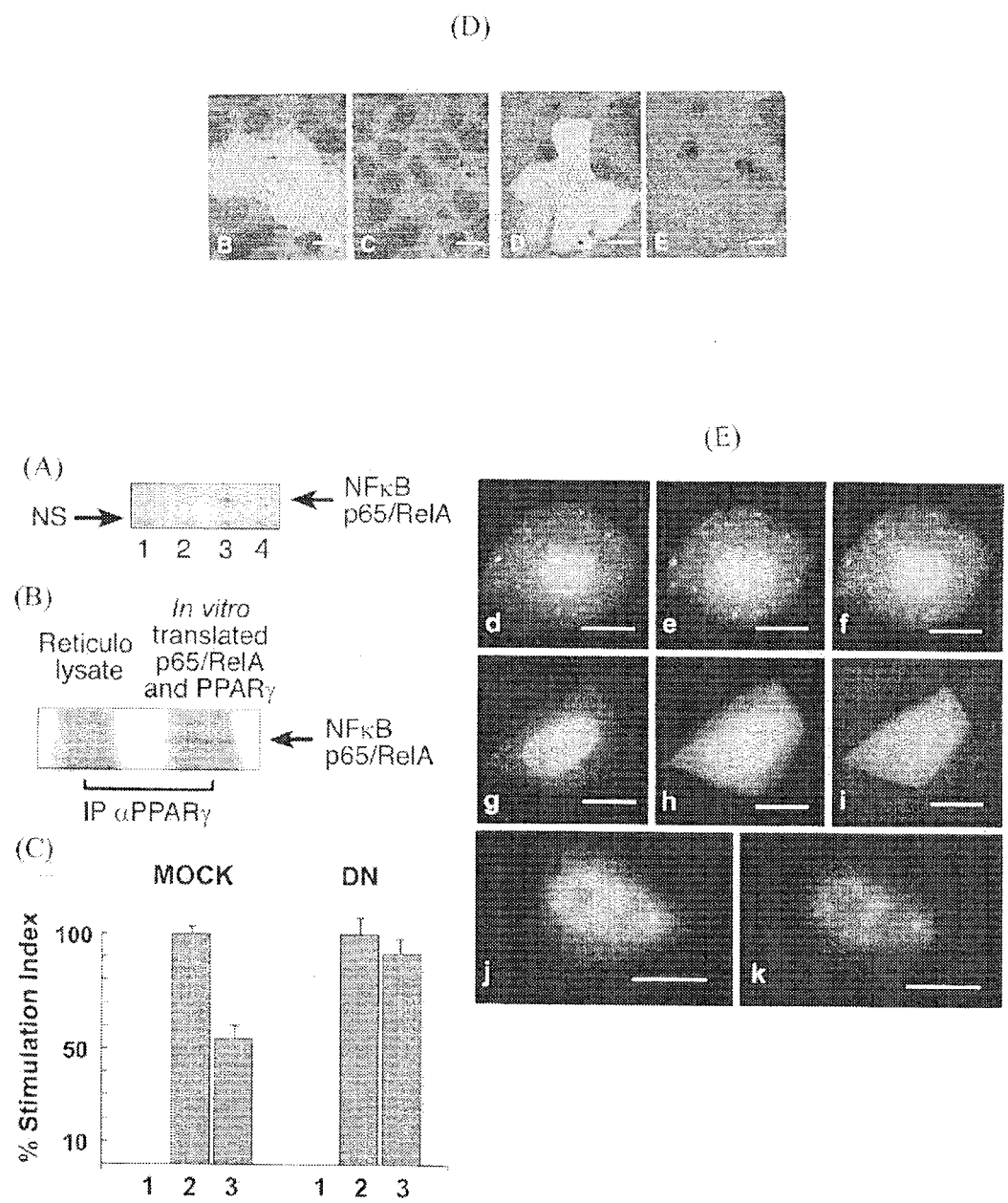

The PPARs are emerging as important modulators of inflammatory processes (Nakajima et al, 2001). PPARs are ligand activated transcription factors that regulate gene expression by binding with retinoid X receptor (RXR), as heterodimeric partners, to specific DNA sequence elements termed PPAR response elements (PPRE). Recent work however, suggests that ligand activation of PPARγ may be important in modulating AP-1 and NF-κB-mediated gene expression (Su et al, 1999). We investigated the role of PPARs in the regulation of NF-κB by *B. thetaiotaomicron*. Consistent with receptor activation we were able to shown that the mRNA for PPARα and PPARγ decreased in cells exposed to both *S. enteritidis* and *B. thetaiotaomicron* (FIG. 4A) and also following exposure to a specific PPARγ ligand, 15-deoxy-$\Delta^{12, 14}$-prostaglandin $J_2$ (15d-$PGJ_2$) but not with fenofibrate, a specific PPARα ligand (FIG. 5B). PPARγ activation has previously been associated with down-regulation of PPARγ mRNA and protein in 3T3-L1 adipocytes (Camp et al, 1999). Using 15d-$PGJ_2$ and ciglitazone we also demonstrated that the activation of inflammatory cytokine expression by *S. enteritidis* could be attenuated over a concentration range considered to be physiological (FIG. 4C, D). Two different ligands for PPARγ were tested as 15d-$PGJ_2$ can inhibit I KappaB Kinase directly (Straus et al, 2000). Both 15d-$PGJ_2$ and ciglitazone have been reported to inhibit AP-1 and COX-2 induction in human intestinal epithelial cells (Subbaramaiah et al, 2001) and may also have therapeutic benefit in the treatment of colitis (Su et al, 1999). We found that PPARγ and PPARα ligands were able to attenuate Salmonella-medicated cytokine induction (FIG. 4C, D, E). This is consistent with recent reports on PPARγ agonists, which have been shown to attenuate NK-κB and IL-8 expression in *H. pylori* treated gastric epithelial cells (Gupta et al, 2001), and also inhibit the infiltration of PMN in ischemia reperfusion-induced intestinal injury (Nakajima et al, 2001).

Although we observed effects with PPARγ and PPARα agonists, in subsequent experiments we concentrated on PPARγ as it has been shown to be expressed at much higher levels than PPARα in the colonic mucosa (Mansen et al, 1996; Fajas et al, 1997).

In addition to regulating gene transcription via PPRE, PPARs have recently been shown to inhibit gene transcription by interfering with other transcription factor pathways through a mechanism independent of DNA binding (Delerive et al, 1999). PPARγ2 can be found in both cytosolic and nuclear compartments (Thuillier et al, 1998), although the physiological relevance of cytosolic PPARγ is currently unknown. Using immunocytochemical localisation on fixed Caco-2 cells we found that *S. enteritidis* induced nuclear accumulation of PPARγ (FIG. 2F). It is important to note that phosphorylation of the $NH_2$-terminal domain of PPARγ (at Ser-122) by MAP kinase, reduces ligand binding affinity and negatively regulates the transcriptional and biological functions of PPARγ (Shao et al, 1998). This would explain why the nuclear accumulation of PPARγ, during the early stages of an inflammatory response to Salmonella, is ineffective in quenching inflammatory gene transcription. Following co-culture of *S. enteritidis* with *B. thetaiotaomicron*, PPARγ redistributed to the cytosol (FIG. 2G, H). The differential distribution of PPARγ within Caco-2 cells exposed to *S. enteritidis* and in the context of *B. thetaiotaomicron* was also demonstrated by western blotting using nuclear and cytoplasmic extracts (FIG. 4F).

All published data relating to PPARγ have focused however, on its nuclear site of action. Using immunocytochemistry we found that *S. enteritidis* induced nuclear accumulation of PPARγ in Caco-2 cells (FIG. 4H(g)). In contrast, PPARγ redistributed to the cytosol following co-culture with *S. enteritidis* and *B. thetaiotaomicron* (FIG. 4H(h,i)). Time course studies indicated that this process was clearly evident at 60 min following exposure to bacteria and was virtually complete by 2 h (results not shown). The differential distribution of PPARγ in Caco-2 cells exposed to *S. enteritidis* and *B. thetaiotaomicron* was also demonstrated by western blotting of nuclear and cytoplasmic extracts (FIG. 4F).

The Salmonella-induced PPARγ protein formed a heterodimeric complex with RXRα (demonstrated by IP, results not shown) and partitioned to the detergent insoluble cell fraction whereas that induced by *B. thetaiotaomicron* was detergent soluble (FIG. 4F). The nucleocytoplasmic shuttling of PPARγ, induced by co-culture of *S. enteritidis* and *B. thetaiotaomicron*, was not blocked by leptomycin B (LMB) treatment (results not shown) and hence not facilitated by the export receptor crm-1 analogous to other nuclear receptors (Bunn et al. 2001). Chilling and metabolic inhibitors did however significantly reduced nuclear export (results not shown). Other biological inhibitors such as TSA (histone deacetylase inhibitor) (FIG. 4H(j-m)) and SB (p38 MAP kinase inhibitor) (data not shown) were also applied to *S. enteritidis*-treated Caco-2 cells and were shown to induce punctate cytosolic labeling and export of PPARγ from the nucleus (FIG. 4H(k)), thus mimicking the *B. thetaiotaomicron* effect. AP-1 signaling pathways, including p38, were not inhibited by *B. thetaiotaomicron* (results not shown), indicating that acetylation/deacetylation reactions are potentially relevant to the PPARγ nuclear export mechanism.

Furthermore, even though PPARγ and PPARα ligands attenuate the Salmonella mediated cytokine induction (results not shown), the PPAR ligands tested in these experiments did not mimic the *B. thetaiotaomicron* effect on PPARγ cellular re-localisation, suggesting a novel endogenous ligand or mechanism of regulation for PPARγ.

Using dual label immunocytochemistry we found that much of the PPARγ protein co-localized with RelA (FIG. 4H n-p). We hypothesise that physical coupling between PPARγ and RelA is an important factor facilitating cytoplasmic localisation in intestinal cells, exposed to *S. enteritidis* and *B. thetaiotaomicron*

It has been suggested that nuclear PPARγ and NF-κB can form an inactive complex (Ricote et al, 1999). Furthermore, glutathione S-transferase pull-down experiments demonstrate that PPARα physically interacts with c-Jun and RelA p65 (Delerive et al, 1999). In our study, using immuno-purification (IP) protocols we show that isolation of PPARγ from cells treated with *S. enteritidis* in the presence of *B. thetaiotaomicron* resulted in the co-purification of RelA (FIG. 4G) suggesting that the proteins are physically associated, possibly as components of a layer multi-protein complex. Direct interaction of PPARγ and RelA was confirmed by in vitro translation and IP (FIG. 4*b*).

Example 5

To further investigate the importance of PARRγ in the regulation of RelA we utilised a dominant negative (DN) form of the receptor (gifted by Professor Chatterjee, University of Cambridge, UK) (Gurnell et al, 200). Within the PPAR receptors there is still a striking conservation of both leucine and glutamic acid. These residues are essential for ligand binding and recruitment of nuclear co-activators. Mutation of these residues generates a DN form of the receptor, which impairs its ability to recruit co-activators and release two co-repressors, silencing mediator of retinoid and thyroid receptors (SMRT) and nuclear co-repressor (NcoR) (Gurnell et al, 2000). Co-immunoprecipitation experiments with DN PPARγ indicate that the SMRT interacts with the receptor in vivo and that the mutated PPARγ is a potent transcriptional repressor. Chimeric fluorescent protein constructs of human PPARγ and the dominant negative form of PPARγ containing a cyan fluorescent protein (CFP) on the carboxyl-terminal domain were prepared by PCR amplification from previously reported clones (Gurnell et al. 2000). Chimeric RelA linked to YFP was gifted from Dr J Schmid (Schmid et al. 2000). Confirmation of successful expression was performed by Western blot analysis of transiently transfected Hela cells using anti-human PPARγ and anti-human RelA antibodies.

Double transfection studies with PPARγ DN and an NF-κB luciferase reporter (gifted by Dr Israel, Pasteur Institute, Paris, France) were performed. Consistent with a recent report we found that cells exposed for long periods to pathogenic *S. enteritidis* inactivated luciferase activity (Savkovic et al, 2000). To avoid this we stimulated the cells for 2 hours and then removed the bacteria by washing and determined luciferase protein production after 8 hours. We found both in the control and PPARγ DN transfected cells, that *S. enteritidis* induced NF-κB activation and luciferase protein synthesis ($P<0.001$) (FIG. 5C). In the PPARγ wild type (NT) transfected cells (luciferase alone) this response was attenuated by *B. thetaiotaomicron* ($P<0.028$), but not in dominant negative (DN) transfected cells (FIG. 5C). Similarly, there was modification of the cellular distribution of RelA, as determined using immunocytochemistry and laser scanning confocal microscopy (LSCM), in cells transfected with green fluorescent protein (GFP) with and without PPARγ DN. In the control cells (GFP alone) the distribution of RelA was predominantly cytosolic as described above for non-transfected cells (FIG. 5D (insert B,C)). In PPARγ DN transfected cells, the distribution was irregular and RelA localised to both the cytosolic and nuclear compartments (FIG. 5D, (insert D, E)). These data demonstrate that PPARγ is essential in sequestering RelA and in preventing nuclear translocation.

We further investigated the cellular distribution of PPARγ and RelA using fluorescent microscopy performed in Caco-2 cells and Hela cells transfected with chimeric constructs of WT and DN PPARγ and CFP and chimeric YFP and RelA. Much of the expressed PPARγ/RelA protein was localized within the nuclei of transfected cells as previously reported (Schmid et al. 2000). Similarly, in cells transfected with PPARγ WT and RelA the predominant expression was nuclear but there was also very clear evidence of punctate cytosolic labeling and co-localization of PPARγ and RelA following incubation with B. thetaiotaomicron (FIG. 5E(f)). In PPARγ DN transfected cells however, RelA was absent from the cytosolic compartment (FIG. 5E(i)). These results indicate that nuclear export of the DN PPARγ, and co-associated RelA, was impaired and it is concluded that PPARγ is essential for both the nuclear export and cytosolic distribution of RelA induced in intestinal cells by B. thetaiotaomicron. In both Caco-2 and Hela cell transfection experiments a significant nuclear pool of expressed PPARγ and RelA protein was observed. In this scenario, irrespective of WT or DN status, aggregates of PPARγ and RelA were clearly visible in the nucleus of cells cultured in the presence of S. enteritidis and B. thetaiotoamicron (also confirmed by IP, results not shown) proving that the PPARγ and RelA interaction occurs within the nuclear compartment. We noted that the distribution of PPAR and RelA within the nucleus was similar to that of splicing factors that occur within nuclear speckles or spliceosomes. In co-localization studies, we found that PPARγ protein co-localized with SC35, a specific pre-mRNA splicing factor, (FIG. 5E(k)) indicating that the PPARγ/RelA complex may also be capable of interacting with the mRNA machinery of the cell. Evidence for the interaction between nuclear receptors and splicing compartments was published during preparation of this manuscript (Zhoa et al. 2002). Clearly, in Caco-2 cells the presence of B. thetaiotaomicron induces enhanced nuclear export of PPARγ and, in a piggy-back fashion the export of transcriptionally active RelA, thereby preventing further nuclear import and RelA-mediated transcription during sustained inflammation. By this mechanism B. thetaiotaomicron exerts a potent anti-inflammatory effect.

The existence of bacteria within the gastrointestinal tract that actively suppress inflammation seems certain. A shift in the balance between enteric microorganisms that suppress inflammation and those that support inflammatory responses may be directly relevant to the etiology of inflammatory diseases of the gastrointestinal tract. Hence it is plausible that inflammatory bowel disease is related to the loss of bacterial strains that actively contribute to immune homeostasis and this may also explain why some patients respond to probiotic therapy (Madsen et al, 2001). Equally, dysfunction of PPARs, due to inadequate levels of receptor protein or due to expression of specific allelic variants that enhance susceptibility to inflammatory conditions in the gut, may be highly relevant. This view is further supported by recent published data indicating that heterozygous PPARγ-deficient mice are significantly more susceptible to ischemia-reperfusion-induced intestinal inflammation and injury (Nakajima et al, 2001).

Methods

Reagents

Tissue culture reagents were obtained from Sigma and Invitrogen, Antibodies obtained from Santa Cruz, Molecular probes, New England Biolabs and, molecular reagents obtained from Promega, Invitrogen and Amersham.

i S. enteritidis/B. thetaiotaomicron Co-culture Models

Caco-2 and Hela cells were routinely cultured in 35 mm culture dishes. Typically experiments required incubation of cells with the following four treatments: cells in medium alone (1); cells incubated with $10^8$ S. enteritidis (2); cells incubated with $10^8$ S. enteritidis and $10^9$ Bacteriodes thetaiotaomicron (3); and cells incubated with $10^9$ B. thetaiotaomicron (4). Bacteria were applied for either 2 h or 4 h and removed by extensive washing. Other bacteria and ligands tested included E. coli 0157 H7, B. vulgatus, PMA, IL-1 α/β and TNFα. All experiments were optimised and protocols were based on detailed dose responses and time courses. Transepithelial migration of PMN cells through Caco-2 cell monolayers was determined by MPO assays (Parkos et al. 1991). The Caco-2 cells were incubated for 2 h before the bacteria were removed and replaced with fresh media. Thereafter cells and media derived from the apical compartment were then solubilised in a 1% Triton X-100 and MPO determined.

Cytokine Analyses

Cytokine analyses were undertaken using Clontech macroarray, Northern hybridizations and real-time PCR of RNA isolated from Caco-2 cells. Total RNA and mRNA were isolated, cDNA produced and PCRs were performed under standard conditions. IL-8 protein concentration was determined by ELISA.

EMSA Analysis of NF-κB and AP-1

Nuclear extracts were incubated with single stranded $^{32}$P-labeled oligonucleotide probes containing consensus binding sequences for NF-κB (SEQ ID NO:1 5'-AGT TGA GGG GAC TTT CCC AGG C-3') or AP-1 (SEQ ID NO: 2 5'-CGC TTG ATG AGT CAG CCG GAA-3'), separated by electrophoresis and visualized by autoradiography. EMSA supershifts were performed using specific NF-κB subunit antibodies. Effects of B. thetaiotaomicron on NFκB and AP-1 signaling were determined by EMSA, western blotting (protein and phosphoprotein), promoter-specific reporter analysis and target gene expression (eg. fos and jun).

Immunofluorescence Analysis

Following experimental treatments Caco2 or Hela cells grown on 35 mm culture dishes were fixed in 4% paraformaldehyde and permeabilised in 0.2% Triton X-100/PBS. Cells were incubated for 1 h at room temperature with primary antibodies (1 µg/ml) diluted in PBS containing 1% serum from the species in which the secondary antibody was raised. Secondary antibodies (1 µ/ml) were either Alexa Fluor 594 donkey anti-goat or Alexa Fluor 488 goat anti-rabbit IgG (Molecular Probes) as appropriate. Labelled cells were mounted with Vectorshield (Vector) and examined on a Zeiss Axioskop 50 widefield fluorescence microscope or on a Bio-Rad Radiance2100 laser scanning microscope. Representative digital images were imported into Adobe Photoshop 6.0 for final arrangement.

Construction of Fluorescently-tagged PPAR●

The coding sequence of PPARγ, and a dominant negative mutant of PPARγ (Gurnell et al. 2000), were modified during PCR amplifications to add a Xho I recognition sequence at the 5' end and a Sac II sequence at the 3' end of the products. The amplifications were performed using Pfu DNA polymerase. Products were restricted and cloned into both pECFP-C1 and pEYFP-C1 (Promega). Successful construction was verified by DNA sequencing. Human p65 cloned into pEYFP-C1 was as previously reported (Schmid et al. 2000).

Caco2 or Hela cells were seeded on 35 mm culture dishes grown to 90% confluence and transfected using standard lipofectamine-mediated methods (Invitrogen). After 48 h, bacterial incubations were undertaken as previously described; cells were fixed for 30 min at room temperature in 4% paraformaldehyde in 0.1M sodium phosphate buffer pH 7.4, washed in PBS and examined on a Zeiss Axioskop 50 widefield fluorescence microscope equipped with custom filters (Omega Optical) for CFP and YFP. Representative images were recorded with a Zeiss AxioCam digital camera, processed with Zeiss AxioVision 3.0 software and imported into Adobe Photoshop 6.0 for final arrangement. In some experiments transfected cells were subjected to the immunofluorescence analyses described above.

Example 6

In Vivo Rat Study

The following example was conducted to establish if *B. thetaiotaomicron* could alter the gut function of specific pathogen-free rats and increase their resistance to a pathogen challenge. Bacteroides generally appear in the small intestine at the suckling-weaning transition (Chang et al, 1994; Hooper et al, 2001). The bacterium was therefore given daily to specific pathogen free Hooded Lister rats from weaning (19 d) through to maturity (34-40 days) to ensure that its presence in high numbers during this period of major gut and immune development. At 34 days of age, the rats were orally challenged with *Salmonella enterica* var. Enteritidis S1400.
Methods
Culture of Bacteria:

*B. thetaiotaomicron*, from Deutsche Sammlung von Microorganismen und GmBH (Braunschweig, Germany) was maintained frozen in Wilkins-Chalgren anaerobic agar. It was subcultured into Wilkins-Chalgren anaerobic broth or M10 medium [10 ml in Hungate tubes (Bryant, 1972)] and grown at 37° C. for 48 hours. A sample (0.5 ml) was transferred to fresh media [10 ml in Hungate tubes] and grown at 37° C. for 24 hours. This culture contained around $10^8$-$10^9$ CFU ml$^{-1}$.

Ten ml of *B. thetaiotaomicron* culture was centrifuged (2000 g, 12 min), the pellet was washed with 0.05M phosphate buffered saline pH 7.2 and then resuspended in commercial jelly [10 ml, 37° C., prepared under anaerobic conditions]. The jelly was poured into a sterile petri dish under $CO_2$ and allowed to set at 4° C. Approximately 1 hour later, the jelly was cut into weighed amounts (0.5 g, ~$10^8$ CFU *B. thetaiotaomicron*) and fed to the rats. The bacterium remained viable for at least 6 hours under these conditions. However, usually all jelly was eaten within a few minutes of being placed in the cage.

*Salmonella enterica* serovar Enteritidis S 1400 was originally isolated from poultry infection and has been characterised (Allen-Vercoe and Woodward, 1999). Stocks, maintained on Dorset egg slopes at 4° C., were sub-cultured on to Luria-Bertani agar plates and grown at 37° C. overnight. Five-ten colonies from the plate were inoculated into 10 mls of Luria-Bertani broth and incubated with agitation at 37° C. overnight to give approximately $1\times10^9$ CFU ml$^{-1}$.

Animal studies: The Rowett Research Institute is licensed under the UK Animals (Scientific Procedures) Act 1986. The ethical review committee and the animal welfare unit of the institute and the appropriate governmental inspectorate monitor and review all animal studies. The management and experimental procedures undertaken were approved by the ethical committee and done in strict accordance with the requirements of the Act by staff licensed to carry out such procedures.

Twenty-four male specific pathogen-free Hooded Lister rats (40 g), bred in the small animal unit of the Rowett Research Institute, were weaned at 19 days and immediately transferred to a Class II facility. They were housed individually in metabolism cages (Techniplast, Kettering, UK) within flexi-film isolators (Moredun, Animal Health, Penicuik, UK) for the duration of the study (21 days). Nesting tunnels were provided in each metabolism cage and cages were arranged within the isolators to allow sight of but not contact with other animals. Sterile distilled water was available at all times. Rats were weighed daily and faeces was collected throughout the study.

Experiments were undertaken at least 3 times with similar results. Data are the means ISD (n=3). The rats were initially given free access to a high quality semi-synthetic (100 g protein kg$^{-1}$) lactalbumin-based diet (Grant et al, 2000). When they reached approximately 80 g (around 30 days old) their food intake was gradually reduced over a 3-4 day period to 7 g rat$^{-1}$ day$^{-1}$, given as two feeds over the day, and then maintained at this level for the remainder of the study. This was the average daily free intake observed for rats of the same age after oral infection with *Salmonella enterica* var. Enteritidis and around 70% of the free intake of this diet by non-infected animals. The rats were housed and managed in this manner from weaning to reduce environmental exposure to bacteria and cross-contamination post-weaning (Grant, 1996).

Twelve of the rats were given *B. thetaiotaomicron* (approximately $10^8$ CFU) once daily from weaning (19d) through to completion of the study. At 34 days of age, six rats pre-treated with *B. thetaiotaomicron* and six controls were given, by gavage, a single dose of 0.8 ml of Salmonella serovar Enteritidis S1400 culture (approximately $10^9$ CFU). The remaining rats were given the equivalent amount of culture medium. All rats were returned to their cages and fed lactalbumin-based diet (7 g rat$^{-1}$ day$^{-1}$) for a further 6 days. On the final day, the rats were fed 2 g of diet and were killed by halothane (Rhone Merieux, Essex, UK) overdose and exsanguination exactly two hours later. The abdomen was opened and tissues were aseptically removed.

The stomach and the small intestine were flushed with phosphate buffered saline (PBS, pH 7.2) to remove contents and non-adherent bacteria. Ten cm of jejunum (5-15 cm from the pylorus) and 10 cm of ileum (5-15 cm from the ileo-caecal junction) were removed. These and the stomach tissue, caecum plus contents, colon plus contents, mesenteric lymph node, a representative proportion of the liver and spleen (200-400 mg) and one kidney were processed for viable counts.

Further pieces of jejunum and ileum (15-25 cm from the pylorus and 15-25 cm from the ileo-caecal junction respectively) were collected and frozen in liquid nitrogen for biochemical analysis, as was the remaining small intestine tissue (~40 cm), liver, spleen, kidney, thymus, lungs, heart and gastrocnemius hind-limb muscles. These were weighed, freeze-dried and reweighed.
Viable Bacteria in Rat Tissues Tissue samples were weighed and then homogenised in Maximum Recovery Diluent (MRD, Fisher Scientific, UK) using a Janke-Kunkel Ultra-Turrax T25 tissue homogeniser at 20,000 rev min$^{-1}$ for 30 seconds. Up to six sequential dilutions (1:10 v/v) of the primary homogenate were made in MRD. Samples of each dilution were plated onto the surface of well-dried XLD agar (Fisher Scientific, UK) and MacConkey agar No. 3 (Fisher Scientific, UK) plates and incubated overnight at 37° C. Viable counts were estimated by the method of Miles and Misra (1938) or by a spread plate method (Collins and Lyme, 1989).
PCR DNA was extracted and purified using a QIAamp DNA Stool Mini Kit (Qiagen Ltd, Crawley, UK). The PCR was based on the method of Teng et al. (2000). The primer pair: SEQ ID No: 3 5'-TGGAGTTTTACTTTGAATGGAC-3'

(BTH-F) and SEQ ID No: 4 5'-CTGCCCTTTTACAATGGG-3' (BTH-R), identified by Teng et al. (2000), were purchased from Sigma-Genosys Ltd (Cambridge, UK). The reaction mixture (50 µl), based on reagents from a Taq PCR Core Kit (Qiagen Ltd, Crawley, UK), contained 50 pmol of both primers, 10 nmol dNTP mixture, 5 µl of 10× Qiagen PCR buffer, 10 µl 5× Q-Solution, 10 µl sample and 1.25 U Taq DNA Polymerase. A hot-start PCR program was used. Reaction mix without Taq DNA Polymerase was heated at 94° C. for 15 seconds and Taq DNA Polymerase was added. The mix was then put through 35 cycles of 94° C. for 10 seconds, 55° C. for 30 seconds and 74° C. for 1 minute, followed by 1 cycle of 74° C. for 2 minutes and 45° C. for 2 seconds. Amplicons were separated on an agarose gel (10 g/l) containing ethidium bromide (1 µg/ml gel). A single amplicon (721 bp) was obtained with DNA from faeces and *B. thetaiotaomicron*. The sequences of these amplicons appeared identical to each other and to the published sequence (Teng et al, 2000).

MPO

Tissue samples were homogenised (1:80 w/v) in ice-cold 5 mM potassium phosphate buffer pH 6.0 using a Janke-Kunkel Ultra-Turrax T25 tissue homogeniser at 20,000 rev min$^{-1}$ for 30 seconds and centrifuged (3000 g×30 min, 4° C.). The pellet (1:20 w/v) was sonicated (3×5 sec) in ice-cold 0.5M potassium phosphate pH 6.0 containing hexadecyltrimethylammonium bromide (HETAB, 5 g/l) and ethylenediaminetetraacetic acid (EDTA, 3.72 g/l), left on ice for 30 min and centrifuged (3000 g×30 min, 4° C.) [Stucchi et al, 2000]. The supernatant was frozen until assayed. Myeloperoxidase (MPO) activity was determined by monitoring $H_2O_2$ dependent oxidation of 3,3',5,5'-tetramethylbenzidine (TMB, Dynex Technologies, Ashford, UK) in 50 mM potassium phosphate buffer pH 6.0 (Zimmerman and Granger, 1990). Absorbance at 450 nm was measured after termination of the reaction with 0.18M $H_2SO_4$. Human myeloperoxidase (Calbiochem, UK) was used as a standard and values were expressed as MPO equivalents.

Immunoreactive MPO in intestinal contents or faeces was determined by a competitive ELISA method. Microtiter plates (Immulon 4, Dynex Technologies, Ashford, UK) were coated [10 ng/well] with human myeloperoxidase in 10 mM phosphate buffered saline pH 7.4 [PBS] overnight at 4° C. After washing [PBS containing Tween-20 (1 ml/l], plates were blocked with PBS containing bovine serum albumin (BSA, 10 g/l) for 1 hour at room temperature. Plates were washed and samples or standards added [50 µl/well] and serially diluted in PBS containing BSA (1 g/l), Tween-20 (1 ml/l) and leupeptin (1 mg/l). Rabbit anti-human myeloperoxidase antibody [Calbiochem, UK, 50 µl/well of 1:4000 dilution] was also added. The plates were incubated for 1 hour, washed and then reacted for 1 hour with biotinylated anti-rabbit IgG followed by Extravidin/peroxidase (EXTRA-3 kit, Sigma-Aldrich, Poole, UK). After washing, TMB reagent (7 µl/well) was added and incubated in the dark for up to 2 hours. The reaction was stopped by addition (50 µl/well) of 0.18M $H_2SO_4$ and the absorbance read at 450 nm. Values were expressed as immunoreactive MPO equivalents.

IgG

IgG was determined by competitive ELISA. Microtiter plates were coated [1 µg/well] with rat IgG (Sigma-Aldrich, Poole, UK) in PBS overnight at 4° C. After blocking and washing of the plates, samples or rat IgG standards [50 µl/well] were added and serially diluted in PBS containing BSA (1 g/l) and Tween-20 (1 ml/l). Biotinylated anti-rat IgG antibodies (Sigma-Aldrich, Poole, UK; 50 µl/well of 1:1000 dilution) were also added and the plates incubated for 1 hour. Plates were then reacted with Extravidin/peroxidase and TMB reagent as per MPO immunoassay. Values were expressed as IgG equivalents.

IgA

IgA was determined by capture ELISA. Microtiter plates were coated with goat anti-rat IgA (Sigma-Aldrich, Poole, UK; 100 µl/well of a 1:100 dilution in PBS) overnight at 4° C. After blocking and washing of the plates, samples or standards [100 µl/well] were added, diluted in PBS containing BSA (1 g/l), Tween-20 (1 ml/l) and leupeptin (1 mg/l) and incubated for 1 hour. After washing, plates were incubated with mouse anti-rat IgA antibodies (Sigma-Aldrich, Poole, UK; 1:500 dilution) for 1 hour, rewashed and incubated with biotinylated anti-mouse IgG antibodies (1:1000 dilution) for a further 1 hour. Plates were then processed as per MPO immunoassay. Values were expressed as IgA equivalents.

LPS-Specific IgG and IgA

Microtiter plates were coated with lipopolysaccharide (LPS; 10 µg/well) from *Salmonella enteritidis* (Sigma Aldrich, Poole, Dorset). After blocking and washing, samples or standards [100 µl/well] were added. Plates were washed onehour later, biotinylated anti-rat IgG or anti-rat IgA was added and the plates were then processed as above. One unit of LPS-specific antibodies was defined as that contained in the volume (µl) giving an absorbance of at least 0.2 in the ELISA. The positive control was sera collected from rats 22 days after infection with SE: LPS-IgA, $3.2 \times 10^4$ units/ml; LPS-IgG, $1.7 \times 10^5$ units/ml.

Elastase

Freeze dried faeces or intestine contents were extracted (1:10 w/v) in ice-cold 0.5M potassium phosphate pH 6.0 containing HETAB, EDTA and $NaN_3$ (1 g/l), left on ice for 30 min, centrifuged (3000 g, 30 min, 4° C.) and the supernatants were frozen.

Sample or leukocyte-elastase (Sigma-Aldrich, Poole, UK) was serially diluted in 0.2M Tris HCl pH 8.0 containing 1 M NaCl and leupeptin (1 mg/l) on a microtiter plate. Substrate (N-succinyl-ala-ala-val-p-nitroanilide, 0.2 g/l, Sigma-Aldrich, Poole, UK) was added and the absorbance at 405 nm monitored immediately and at intervals up to 20 hours during incubation at 37° C. Values were expressed as leukocyteelastase equivalents.

DNA, RNA, Protein

DNA, RNA, protein were determined as before by the diphenylamine, orcinol and modified Lowry methods (Grant et al, 2000). Salmon testes DNA, yeast RNA and bovine serum albumin were used as standards.

Statistical Analysis

Data were assessed by one way analysis of variance (ANOVA) in combination with the Tukey multiple comparison test using the Instat Statistical Package (GraphPad Software Inc., San Diego, USA).

Results

*Bacteroides thetaiotaomicron* (BT) was detected in faeces samples collected from BT-treated rats. BT was also found in faeces of control rats. However, the levels (equivalent of approximately $10^4$ CFU/g faeces) were below those found in faeces from rats treated daily with BT (equivalent of approximately $10^6$ CFU/g faeces).

Body weight gains, major organ weights and small intestine and liver compositions for BT rats were similar to those for controls (Tables 1-4). The general distribution of lactose fermentors and non-lactose fermentors in the gastrointestinal tract seemed to be unaffected and, as with controls, no lactose fermentors or non-lactose fermentors bacteria were detected in mesenteric lymph node, liver, spleen or kidney samples. In addition, the levels of non-specific IgA, elastase, and immunoreactive MPO in intestinal contents and faeces, MPO in intestine tissue and non-specific IgG and IgA in serum were comparable to those samples collected from control animals.

TABLE 1

Bacterial numbers ($Log_{10}$ CFU/g) associated with tissues taken from control rats or rats orally treated with *Bacteroides thetaiotaomicron* [BT], *Salmonella enterica* var. enteritidis [SE] or *S. enteritidis* plus *B. thetaiotaomicron* [SE + BT].

|  | Stomach | Jejunum | Ileum | Caecum | Colon | MLN | Liver | Spleen | Kidneys |
|---|---|---|---|---|---|---|---|---|---|
| Salmonella[1] | | | | | | | | | |
| SE | 4.90 ± 0.27 | 5.04 ± 0.54 | 5.87 ± 0.90 | 6.84 ± 0.78 | 6.45 ± 1.03 | 5.43 ± 0.21 | 3.08 ± 0.46 | 3.77 ± 0.25 | ND |
| SE + BT | 5.06 ± 0.33 | 5.15 ± 0.54 | 6.23 ± 0.12 | 8.06 ± 0.81* | 7.04 ± 0.87 | 5.24 ± 0.44 | 2.34 ± 0.36* | 3.04 ± 0.32* | ND |
| Lactose fermentors | | | | | | | | | |
| Control | 4.97 ± 1.18 | 3.27 ± 0.66 | 4.90 ± 0.97 | 8.08 ± 0.63 | 7.68 ± 0.58 | $ND^a$ | $ND^a$ | $ND^a$ | ND |
| BT | 3.90 ± 0.84 | 2.78 ± 0.19 | 4.15 ± 1.13 | 7.14 ± 1.40 | 7.15 ± 1.14 | $ND^a$ | $ND^a$ | $ND^a$ | ND |
| SE | 3.88 ± 0.69 | 3.13 ± 0.55 | 4.01 ± 1.00 | 7.26 ± 0.64 | 6.71 ± 0.35 | $3.49 ± 0.91^b$ | $1.85 ± 0.85^b$ | $1.96 ± 1.07^b$ | ND |
| SE + BT | 4.16 ± 0.66 | 3.11 ± 0.63 | 4.39 ± 1.34 | 8.32 ± 0.68 | 7.42 ± 0.95 | $3.73 ± 0.90^b$ | $1.41 ± 0.20^b$ | $1.83 ± 0.56^b$ | ND |
| Non-lactose fermentors | | | | | | | | | |
| Control | $3.92 ± 1.12^a$ | $3.15 ± 0.57^a$ | $3.88 ± 0.98^a$ | 6.73 ± 1.06 | 6.54 ± 0.74 | $ND^a$ | $ND^a$ | $ND^a$ | ND |
| BT | $3.80 ± 0.20^a$ | $2.82 ± 0.29^a$ | $4.46 ± 0.85^a$ | 6.69 ± 0.95 | 6.63 ± 0.66 | $ND^a$ | $ND^a$ | $ND^a$ | ND |
| SE | $5.02 ± 0.42^b$ | $4.73 ± 0.59^b$ | $6.21 ± 0.36^b$ | 7.10 ± 0.56 | 6.48 ± 0.66 | $5.22 ± 0.30^b$ | $3.16 ± 0.58^b$ | $3.81 ± 0.22^b$ | ND |
| SE + BT | $5.12 ± 0.23^b$ | $4.98 ± 0.72^b$ | $6.24 ± 0.85^b$ | 8.01 ± 0.62* | 7.26 ± 0.90 | $5.41 ± 0.29^b$ | $2.47 ± 0.23^{c*}$ | $3.27 ± 0.23^{c*}$ | ND |

Means ± SD, n = 6, samples collected 6 d post-infection with *S. enteritidis*. *SE + BT differs significantly from SE (p ≦ 0.05). For lactose fermentors and non-lactose fermentors values in a column with distinct superscripts differ significantly (p ≦ 0.05). ND, not detected. The limit of detection was 2.7 except for liver spleen and kidneys for which it was 1.3. [1]No salmonella, lactose fermentors or non-lactose fermentors were detected in MLN, liver, spleen or kidneys of control or BT rats.

*S. enteritidis* [SE] was found throughout the gastrointestinal tract six days after oral challenge (Table 1). In addition, they were detectable in the mesenteric lymph node, liver and spleen. Total non-lactose fermentors had a similar tissue distribution in these rats (Table 1). The numbers of lactose fermentors in the gut did not appear to be affected by salmonella infection. However, significant numbers of lactose fermentors did appear in the mesenteric lymph nodes, liver and spleen of SE-infected rats (Table 1).

The numbers of viable salmonella detected in the liver and spleen after challenge with salmonella were greatly reduced if rats had also been treated with *B. thetaiotaomicron* [SE+BT] (Table 1). Total non-lactose fermentors in these tissues were also lowered but lactose fermentor numbers were unchanged. The levels of salmonella, total non-lactose fermentors and lactose fermentors throughout the gastrointestinal tract and in the mesenteric lymph node were similar for SE+BT and SE (Table 1). In addition, faecal excretion of salmonella over the 6 day experiment occurred at comparable rates in pathogen-infected rats (SE+BT, 7.0±0.8 $Log_{10}$CFU/g $d^{-1}$, SE, 6.2±0.6 $Log_{10}$CFU/g $d^{-1}$).

TABLE 2

Weights (mg wet weight/100 g fresh body weight) of tissues taken from control rats or rats orally treated with *Bacteroides hetaiotaomicron* [BT], *Salmonella enterica* var. enteritidis [SE] or *S. enteritidis* plus *B. thetaiotaomicron* [SE + BT].

|  | Control | BT | SE | SE + BT |
|---|---|---|---|---|
| Intake (g/d) | 7.0 | 7.0 | 7.0 | 7.0 |
| Initial weight (g) | 83 ± 2 | 83 ± 3 | 86 ± 3 | 88 ± 2 |
| Final weight (g) | 93 ± 3 | 94 ± 2 | 98 ± 4 | 100 ± 3 |
| Stomach | 887 ± 64 | 831 ± 82 | 965 ± 74 | 846 ± 149 |
| Jejunum (20 cm) | $705 ± 133^a$ | $759 ± 78^a$ | $1035 ± 224^b$ | $966 ± 121^b$ |
| Ileum (20 cm) | $540 ± 46^a$ | $576 ± 66^a$ | $1139 ± 251^b$ | $999 ± 168^b$ |
| Small intestine | $2979 ± 255^a$ | $3074 ± 282^a$ | $5021 ± 420^b$ | $4425 ± 415^{c*}$ |
| MLN | $105 ± 48^a$ | $100 ± 40^a$ | $484 ± 153^b$ | $325 ± 73^b$ |
| Spleen | $237 ± 38^a$ | $228 ± 31^a$ | $315 ± 26^b$ | $325 ± 50^b$ |
| Liver | $3773 ± 72^a$ | $3778 ± 239^a$ | $4409 ± 266^a$ | $4353 ± 166^b$ |
| Kidneys | 886 ± 35 | 906 ± 28 | 875 ± 29 | 926 ± 62 |
| Thymus | 337 ± 32 | 324 ± 39 | 355 ± 63 | 339 ± 29 |
| Lungs | 744 ± 43 | 698 ± 97 | 767 ± 65 | 756 ± 82 |
| Heart | 482 ± 73 | 442 ± 18 | 437 ± 27 | 450 ± 44 |
| Gastrocnemius muscles | $814 ± 24^a$ | $834 ± 22^a$ | $753 ± 35^b$ | $838 ± 47^{a*}$ |

Means ± SD, n = 6, samples collected 6d post-infection with *S. enteritidis*.
MLN, mesenteric lymph nodes.
Values in a row with distinct superscripts differ significantly (p ≦ 0.05).
*SE + BT differs significantly from SE (p ≦ 0.05).

TABLE 3

Weight and composition (mg) of tissues taken from control rats or rats orally treated with *Bacteroides thetaiotaomicron* [BT], *Salmonella enterica* var. enteritidis [SE] or *S. enteritidis* plus *B. thetaiotaomicron* [SE + BT].

|  | Control | BT | SE | SE + BT |
|---|---|---|---|---|
| Jejunum (20 cm) | | | | |
| Wet weight | 650 ± 99$^a$ | 712 ± 68$^a$ | 1006 ± 198$^b$ | 956 ± 89$^b$ |
| Water | 526 ± 76$^a$ | 588 ± 66$^a$ | 824 ± 178$^b$ | 748 ± 86$^b$ |
| Dry weight | 124 ± 34$^a$ | 136 ± 24$^a$ | 182 ± 24$^b$ | 208 ± 32$^b$ |
| MPO (μg) | 20.7 ± 5.8 | 29.3 ± 5.2 | 24.7 ± 9.4 | 34.4 ± 10.9 |
| Ileum (20 cm) | | | | |
| Wet weight | 500 ± 47$^a$ | 540 ± 51$^a$ | 1104 ± 196$^b$ | 991 ± 159$^b$ |
| Water | 425 ± 57$^a$ | 458 ± 83$^a$ | 903 ± 74$^b$ | 785 ± 70$^{c*}$ |
| Dry weight | 74 ± 26$^a$ | 82 ± 42$^a$ | 201 ± 26$^b$ | 206 ± 45$^b$ |
| MPO (μg) | 24.7 ± 4.2$^a$ | 33.1 ± 6.2$^a$ | 94.4 ± 9.5$^b$ | 48.7 ± 14.9$^{c*}$ |
| Total small intestine | | | | |
| Wet weight | 2756 ± 139$^a$ | 2883 ± 89$^a$ | 4885 ± 309$^b$ | 4391 ± 389$^b$ |
| Water | 2098 ± 121$^a$ | 2150 ± 129$^a$ | 3884 ± 212$^b$ | 3273 ± 350$^{c*}$ |
| Dry weight | 658 ± 29$^a$ | 734 ± 50$^a$ | 1002 ± 79$^b$ | 1117 ± 76$^b$ |
| DNA | 3.4 ± 0.8$^a$ | 3.9 ± 0.4$^a$ | 5.5 ± 0.5$^b$ | 6.5 ± 0.9$^b$ |
| RNA | 17.8 ± 2.1$^a$ | 23.6 ± 3.7$^a$ | 30.9. ± 1.2$^b$ | 35.7 ± 5.8$^b$ |
| Protein | 268 ± 29$^a$ | 293 ± 59$^a$ | 480 ± 56$^b$ | 530 ± 84$^b$ |
| Liver | | | | |
| Wet weight | 3520 ± 107$^a$ | 3546 ± 269$^a$ | 4295 ± 268$^b$ | 4344 ± 284$^b$ |
| Dry weight | 1022 ± 59$^a$ | 992 ± 78$^a$ | 1117 ± 94$^a$ | 1078 ± 89$^a$ |
| Spleen | | | | |
| Wet weight | 223 ± 33$^a$ | 207 ± 6$^a$ | 311 ± 35$^b$ | 299 ± 39$^b$ |
| Dry weight | 68 ± 23$^a$ | 59 ± 11$^a$ | 63 ± 14$^a$ | 74 ± 17$^a$ |
| Mesenteric lymph node | | | | |
| Wet weight | 99.0 ± 47.84$^a$ 323.4 ± 68.9$^b$ | 93.5 ± 37.1$^a$ | | 476.2 ± 165.5$^b$ |
| Water | 63.5 ± 21.6$^a$ 208.5 ± 40.0$^b$ | 66.5 ± 26.0$^a$ | | 304.1 ± 115.2$^b$ |
| Dry weight | 35.5 ± 29.3$^a$ 114.9 ± 34.0$^b$ | 27.0 ± 16.6$^a$ | | 72.1 ± 72.7$^b$ |

Means ± SD, n = 6, samples collected 6d post-infection with *S. enteritidis*.
Values in a row with distinct superscripts differ signficantly (p ≦ 0.05).
*differs significantly from SE (p ≦ 0.05).
ND, not detected.

The weight of the small intestine was increased as a result of salmonella infection (Tables 2,3). This was most marked in the ileal tissue and appeared to be due to accumulation of water and increases in the protein, RNA and DNA content of the tissue (Table 3). Treatment with BT slightly modified the response to infection. Thus, the water content of small intestine from SE+BT [748±22 mg/g] was considerably lower than that in tissue from SE rats [799±17 mg/g]. Indeed, it was similar to the levels in tissue from non-infected rats [BT, 745±24 mg/g controls, 760±10 mg/g]. In contrast, there was no significant difference between SE and SE+BT rats in their small intestine dry weights or DNA, RNA and protein contents.

TABLE 4

Composition of serum, intestine contents or faeces collected from control rats or rats orally treated with *Bacteroides thetaiotaomicron* [BT], *Salmonella enterica* var. enteritidis [SE] or *S. enteritidis* plus *B. thetaiotaomicron* [SE ± BT].

|  | Control | BT | SE | SE + BT |
|---|---|---|---|---|
| Serum | | | | |
| IgA (mg/ml) | 0.19 ± 0.02$^a$ | 018 ± 0.02$^a$ | 0.35 ± 0.06$^b$ | 0.28 ± 0.04$^b$ |
| IgG (mg/ml) | 0.91 ± 0.13 | 0.83 ± 0.17 | 0.89 ± 0.17 | 0.97 ± 0.10 |
| LPS-IgA (units/ml) | ND-800 | ND | ND | ND-800 |
| LPS-IgG (units/ml) | ND | ND | ND | ND |

TABLE 4-continued

Composition of serum, intestine contents or faeces collected from control rats or rats orally treated with *Bacteroides thetaiotaomicron* [BT], *Salmonella enterica* var. enteritidis [SE] or *S. enteritidis* plus *B. thetaiotaomicron* [SE ± BT].

|  | Control | BT | SE | SE + BT |
|---|---|---|---|---|
| Intestinal contents |  |  |  |  |
| Protein (mg) | 7.01 ± 1.75$^a$ |  | 5.32 ± 1.50$^a$ |  |
|  | 11.61 ± 3.15$^b$ |  | 12.89 ± 3.03$^b$ |  |
| IgA (mg) | 0.38 ± 0.18$^a$ | 023 ± 0.14$^a$ |  | 1.19 ± 0.41$^b$ |
|  | 1.42 ± 0.53$^b$ |  |  |  |
| LPS-IgA (units) | ND$^a$ | ND$^a$ | 162 ± 58$^b$ | 221 ± 35$^b$ |
| Elastase (μg) | 1.43 ± 0.29$^a$ | 210 ± 0.38$^a$ | 4.20 ± 0.73$^b$ | 3.10 ± 0.59$^c$ |
| MPO (μg) | 1.86 ± 1.31$^a$ | 270 ± 1.29$^a$ | 6.56 ± 2.20$^b$ | 3.91 ± 1.40$^a$ |
| Faeces |  |  |  |  |
| Dry matter (mg/d) | 369 ± 37$^a$ | 359 ± 37$^a$ | 532 ± 44$^b$ | 553 ± 46$^b$ |
| Water (mg/d) | 183 ± 46$^a$ | 213 ± 41$^a$ | 416 ± 119$^b$ | 412 ± 84$^b$ |
| Protein (mg/d) | 85 ± 15$^a$ | 97 ± 12$^a$ | 162 ± 27$^b$ | 179 ± 17$^b$ |
| IgA (μg/d) | 505 ± 202 | 475 ± 168 | 1412 ± 773 | 1022 ± 638 |
| Elastase (μg/d) | 6.4 ± 0.9$^a$ | 5.7 ± 1.0$^a$ | 12.5 ± 1.5$^b$ | 8.9 ± 1.1$^c$ |
| MPO (μg/d) | 2.5 ± 1.2$^a$ | 2.6 ± 1.0$^a$ | 5.5 ± 1.6$^b$ | 2.9 ± 1.0$^a$ |

Means ± SD, n = 6, samples during 6d post-infection with *S. enteritidis*.
Values in a row with distinct superscripts differ signficantly ($p \leq 0.05$).
*differs significantly from SE ($p \leq 0.05$).
ND, not detected.

Myeloperoxidase (MPO) activity was significantly elevated in ileal tissue collected from SE rats (Table 4). In addition, immunoreactive-MPO and elastase activity in intestinal contents and faeces were also greatly increased (Table 4). In contrast, the levels of these enzymes in equivalent samples from SE+BT rats were similar to or only slightly higher than control samples.

Immunoreactive non-specific IgA in intestine contents, faeces and serum was increased as a result of salmonella infection (Table 4). There were however no differences between SE+BT and SE in these IgA responses. Small amounts of LPS-specific IgA were also detected in the blood and intestine contents. Again, there were no significant differences between SE+BT and SE, although there was a tendency for LPS-specific IgA levels in the intestine to be higher for SE+BT rats.

Gastrocnemius hind-limb muscle weights were significantly lower in SE rats than in controls (Table 2). This was not evident in SE+BT rats and appeared to be a result of a reduced muscle accretion. SE rats deposited approximately 6.6±5.7 mg wet weight [1.4±1.2 mg dry weight] of gastrocnemius muscle per day whereas with SE+BT the accretion rate was 17.1±4.1 mg wet weight [4.2±1.0 mg dry weight] per day. Deposition of this muscle in controls was 15.5±2.9 mg wet weight [3.8±0.7 mg dry weight] per day and 17.0±4.2 mg wet weight [4.2±1.0 mg dry weight] per day in BT rats. This suggests that the SE rats deposited an average of 0.3 g (wet weight) total skeletal muscle daily whilst with SE+BT, BT or control rats the levels were around 0.7-0.8 g daily (FIG. 6).

Liver, spleen and mesenteric lymph node wet weights were significantly elevated in salmonella-infected rates (Table 3). This was due primarily to accumulation of water in the liver and spleen and an increase in both water and dry matter in the mesenteric lymph node (Table 4). Peroxidase activity in the mesenteric lymph node of infected rats was also elevated [SE, 31.0±25.0; SE+BT, 37.7±23.8; BT, 0.9±0.9; control, 0.4±0.3 μg]. There were however no significant differences between the SE and SE+BT groups in these tissue parameters.

Discussion

Salmonellosis: *Salmonella enterica* var. Enteritidis S1400 colonised the whole gastrointestinal tract of rats and translocated to the mesenteric lymph node, liver and spleen. In addition, the wet and dry weight of the small intestine was greatly increased as a result of infection. This was most marked in the ileum and was linked to accumulation of water and higher levels of protein, RNA and DNA in the tissue. The basic characteristics of the infection were therefore similar to those seen for other Enteritidis or *S. enterica* var. Typhimurium strains in the rat models (Naughton et al, 1996; 2001; Ewen et al, 1997; Bovee-Oudenhoven et al, 1999; Islam et al, 2000; Havelaar et al, 2001).

Enteritidis and Typhimurium cause a self-limiting infection in rats, that is localised primarily to the gastrointestinal tract with invasion occurring via the ileum and only limited systemic spread being evidence (Naughton et al, 1996; Bovee-Oudenhoven et al, 1997; 1999; Islam et al, 2000). Furthermore, severe bacteremia and death is rare, unless the health status or gut integrity of the rats has been compromised by other factors prior to infection. This contrasts starkly with salmonellosis in some mouse models in which these strains elicit a severe typhoid-like illness with a high incidence of mortality (Lu et al, 1999; Kingsley and Baumler, 2000; Schechter and Lee, 2000). Thus, salmonellosis in the rat has strong similarities to the self-limiting gastroenteritis-type infections common in humans and domesticated animals infected by Enteritidis or Typhimurium.

In the present study, salmonella infection was found to provoke a strong inflammatory response in the distal but not the proximal small intestine. Thus, the activity of myeloperoxidase (MPO, a neutrophil marker) in ileal tissue was significantly elevated. In addition, levels of immunoreactive-MPO and leukocyte elastase activity in intestinal contents and faeces were increased. This is compatible with infiltration of polymorphonuclear leukocytes and other inflammatory cells into ileal tissue and the exvasion of inflammatory cells into the intestinal lumen, as previously observed in animal models of salmonellosis (Naughton et al, 1995; 1996; Vassiloyanakopoulos et al, 1998; Darwin and Miller, 1999; Henderson et al, 1999). In addition, it is consistent with the ileum being the primary site of colonisation and invasion by salmonella (Carter and Collins, 1974; Naughton et al, 1996).

Non-specific IgA in serum, intestine contents and faeces was significantly increased as a result of salmonella infection. Furthermore, there were indications of development of an LPS-specific IgA response by 6 days post-infection. In addition, faecal dry matter, water and protein outputs were elevated, as were the levels of protein in the intestinal contents. Liver and spleen weights were also increased as a result of the infection.

Salmonellosis was also found to impair skeletal muscle metabolism in rats. The infected animals continued to deposit skeletal muscle but the daily accretion rates were about 40-50% of those observed in controls, despite both sets of rats having the same dry matter (7 g/rat $d^{-1}$) and protein (0.7 g/rat $d^{-1}$) intake. This may have been due to diversion and utilisation of nutrients to support defensive responses against infection (Klasing and Calvert, 1999) and/or the actions of endotoxin or other bacterial factors on muscle protein synthesis (Friman et al, 1984; Lang et al, 2000).

*B. thetaiotaomicron*: In the present study, rats were exposed to high levels of exogenous *B. thetaiotaomicron* throughout a period of rapid growth and maturation of the gut and development of the immune system. Some Bacteroides strains are opportunistic pathogens and would be likely to have deleterious effects during this developmental period. However, as in studies with mature ex-germ-free animals monocontaminated with *B. thetaiotaomicron* (Hooper et al, 1999; 2001; Noack et al, 2000), there were no indications that *B. thetaiotaomicron* adversely affected gut or systemic metabolism of the specific pathogen-free rats. Indeed, all the parameters monitored in rats treated with *B. thetaiotaomicron* alone, including inflammatory markers and immunoglobulin levels, were similar to those obtained for controls.

*B. thetaiotaomicron* and salmonellosis: *B. thetaiotaomicron* modified the nature of the infection caused by Enteritidis S 1400 in rats and reduced its overall severity. In particular, inflammatory responses in the small intestine were limited, the numbers of viable salmonella found in the liver and spleen were greatly reduced and skeletal muscle accretion rates were restored to around control levels. *B. thetaiotaomicron* thus had effects both locally in the gut and at remote systemic tissues.

Some aspects of salmonellosis were however unaffected by *B. thetaiotaomicron*. Enteritidis numbers in the gastrointestinal tract and mesenteric lymph nodes and faecal excretion of the pathogen were unaltered. In addition, the enlargement of the small intestine (increase in dry weight and DNA, RNA and protein content) associated with Enteritidis infection was also evident in rats given *B. thetaiotaomicron* and Enteritidis. This suggests that *B. thetaiotaomicron* does not interfere directly with salmonella itself or block its general effects on host metabolism. Instead, the bacterium may selectively modulate host-responses against infection, possibly targetting those that are potentially detrimental to gut integrity.

A number of bacterial strains have recently been shown to give partial protection against Enteritidis or Typhimurium infection. Some outcompete the pathogen for attachment sites or nutrients in the gut or produce bactericidal compounds. As a result, they reduce the numbers of salmonella found in the intestine and reaching the mesenteric lymph nodes, liver and spleen (Bernet-Camard et al, 1997; Hudault et al, 1997; 2001; Hendriksson and Conway, 2001). In contrast, many have little or no effect on the numbers of salmonella in the gut. However, as with *B. thetaiotaomicron*, they still significantly ameliorate the pathogenic infection (Silva et al, 1999; Filho-Lima et al, 2000; Schu et al, 2000; Hendriksson and Conway, 2001; Maia et al, 2001). Protection given by the latter strains is thus by mechanisms other than competitive exclusion or secretion of bactericidal compounds. Salmonella breach the intestine epithelium by interfering with cell metabolism, cell-cell interactions and host-response mechanisms (Darwin and Miller, 1999; Netea et al, 2000; Eaves-Pyles, 2001; Gewirtz et al, 2001; Lu and Walker, 2001; Ohl and Miller, 2001). In particular, they trigger rapid infiltration of polymorphonuclear leukocytes into the tissue and provoke acute inflammation and severe disruption of the gut (Madara, 1997; Ohl and Miller, 2001). Neutrophil infiltration into the gut is mediated by chemoattractant chemokines, such as IL-8, that are secreted by epithelial cells in response to pathogenic infection (McCormick et al, 1995; Madara, 1997; Darwin and Miller, 1999; Fleckstein and Kopecko, 2001). Release of this chemoattractant was high if epithelial cells were cultured with salmonella in vitro (McCormick et al, 1995; Campbell et al, 2001). In contrast, its output was greatly reduced if the epithelial cells were cultured with salmonella and *B. thetaiotaomicron* in combination (Campbell et al, 2001).

Myeloperoxidase levels in ileal tissue and intestine contents of rats given *B. thetaiotaomicron* and Enteritidis were much lower than in comparable samples from animals dosed with salmonella alone. Thus, the inflammatory responses normally triggered in the intestine by salmonella, were apparently attenuated if animals had also been treated with *B. thetaiotaomicron*. The bacterium may, as found in vitro (Campbell et al, 2001), block salmonella-linked production of chemoattractant chemokines by epithelial enterocytes and thus prevent the recruitment of neutrophils into the tissue. By modulating this host-response in vivo, *B. thetaiotaomicron* may limit the degree of gut inflammation and damage that occurs as a result of infection and thereby preserve gut integrity. This would also reduce the demands of the gut for nutrients to support repair (Klasing and Calvert, 1999) and allow more to go to other tissues, such as the skeletal muscle.

Salmonella drain to the mesenteric lymph nodes, once they pass through the intestinal epithelium (Kingsley and Baulmer, 2000). They may then be cleared from there by macrophages or alternatively break out from the mesenteric lymph nodes and spread to the blood, liver and spleen (Kingsley and Baulmer, 2000; Lu and Walker, 2001). Significant numbers of Enteritidis were detected in the mesenteric lymph nodes, liver and spleen of infected rats. Treatment of animals with *B. thetaiotaomicron* greatly reduced the levels of viable pathogen found in the liver and spleen. However, it did not affect the Enteritidis numbers in the mesenteric lymph nodes. Therefore, *B. thetaiotaomicron* did not appear to limit invasion and drainage of salmonella to this site, despite its major effects on intestinal metabolism. Since pathogen levels were reduced in the systemic tissues, this may indicate that the main protective effects of *B. thetaiotaomicron* arise through changes in systemic metabolism.

Commensal bacteria are potent immuno-modulators (Herias et al, 1999; Talham et al, 1999; Scharek et al, 2000; Isolauri et al, 2001; Lu and Walker, 2001). In particular, treatment of mice with *Bifidobacterium lactis* appeared to enhance their immune function and responsiveness against salmonella (Schu et al, 2000). Phagocytotic activity in blood and peritoneal cells, lymphocyte mitogenic responsiveness and secretion of Typhimurium-specific antibodies were elevated. *B. thetaiotaomicron* may have similar effects on systemic metabolism. The lower numbers of salmonella in the liver and spleen of *B. thetaiotaomicron*-treated rats might therefore be the result of enhanced clearance of the pathogen from the blood and internal organs.

Lactose fermentors (*E. coli*), albeit in low numbers, were also found in the liver and spleen of Enteritidis-infected rats. However, unlike salmonella, the levels of these bacteria were not affected by *B. thetaiotaomicron*. There may therefore be some selectivity in the bacterial clearance promoted by *B. thetaiotaomicron*. Alternatively, because the *E. coli* are derived from the normal flora of the rats, they may not be readily recognised as potentially harmful, even although they are present at inappropriate tissue sites.

*B. thetaiotaomicron* may however reduce systemic spread of salmonella by acting locally on the gut. It is generally accepted that salmonella attach to the gut epithelium, invade through the tissue, drain to the mesenteric lymph nodes and may then spread to the liver and spleen (Kingsley and Baulmer, 2000). However, recent work suggests that systemic spread of the pathogen can occur by an alternative route. Pathogens sampled luminally by dendritic cells or in the subepithelium by CD18-expressing phagocytes may be transferred directly to the liver and spleen, without drainage through the lymphatic system (Varquez-Torres et al, 1999; Isberg and Barnes, 2000; Rescigno et al, 2001). As a result, salmonella found in the liver and spleen are likely to be derived from the two uptake routes. Recruitment of these phagocytes will probably be mediated by chemoattractant chemokines produced by epithelial cells (Izadpanah et al, 2001; Kellennan and McEvoy, 2001). Since *B. thetaiotaomicron* appears to limit neutrophil recruitment and inflammation in the gut by preventing secretion of the necessary chemoattractant chemokines (Campbell et al, 2001), it may also suppress the chemokines required to recruit dendritic cells or CD18-expressing phagocytes and as a result prevent or limit uptake of salmonella by this system.

SUMMARY

Orally administered *B. thetaiotaomicron* reduced the severity of infection caused by Enteritidis in rats. The numbers of viable salmonella in the liver and spleen were greatly reduced, skeletal muscle accretion rates were restored to normal and inflammatory responses in the small intestine were attenuated. This was due possibly to enhanced immune responsiveness and rapid clearance of salmonella at remote sites, such as the liver and spleen. However, it was also, at least in part, a result of local effects of the bacterium on the gut. Neutrophil recruitment and inflammation in the intestine was prevented or delayed by the action of *B. thetaiotaomicron*. It may also have blocked direct uptake of salmonella in phagocytes to the liver and spleen.

REFERENCES

1. E. Cario et al. *J Immunol.* 164, 966 (2000).
2. A. T. Gewirtz, T. A. Navas, S. Lyons, P. J. Godowski, J. L. Madara, *J. Immunol.* 167, 1882 (2001).
3. B. A. McCormick, S. P. Colgan, C. Delp-Archer, S. I. Miller, J. L. Madara, *J. Cell Biol.* 123, 895 (1993).
4. L. Hang et al., *J. Immunol.* 162, 3037 (1999).
5. S. Ghosh, M. J. May, E. B. Kopp *Annu. Rev. Immunol.* 16, 225-260 (1998).
6. M. J. May, S. Ghosh. *Immunol. Today* (1998).
7. Q. Cheng et al., *J. Biol. Chem.* 269, 13551 (1994).
8. P. J. Chiao, S. Miyamoto, I. M. Verma. *Proc. Natl. Acad. Sci.* USA 91, 28-32. (1994).
9. P. Renard et al. *J. Biol. Chem.* 275, 15193 (2000).
10. A. S. Neish et al., *Science* 289, 1560 (2000).
11. T. Meyer-ter-Vehn, A. Covacci, M. Kist, H. L. Pahl, *J. Biol. Chem.* 275, 16064 (2000).
12. J. Raingeaud et al., *J. Biol. Chem.* 270, 7420 (1995).
13. Nakajima et al. *Gastroenterology* 120, 460 2001.
14. E. D. Rosen, B. M. Spiegelman. *J. Biol. Chem.* 276, 37731-37734 (2001).
15. C. G. Su et al., *J. Clin. Invest.* 104, 383 (1999).
16. C. F. Bunn et al., *Mol. Endocrinol.* 15, 512 (2001).
17. M. Ricote, J. T. Huang, J. S. Welch, C. K. Glass, *J. Leukoc. Biol.* 66, 733 (1999).
18. P. Delerive et al., *J. Biol. Chem.* 274, 32048 (1999).
19. M. Gurnell et al., *J. Biol. Chem.* 275, 5754 (2000).
20. S. D. Savkovic, A. Koutsouris, G. Wu, G. Hecht, *Biotechniques* 29, 514 (2000).
21. A. Birbach et al. *J. Biol. Chem.* 277, 10842 (2002).
22. J. Schmid et al. *J. Biol. Chem.* 275, 17035 (2002).
23. Y. Zhoa et al., *J Biol. Chem.* 277, 30031-30039 (2002).
24. K. Madsen et al., *Gastroenterology* 121, 580 (2001).
25. C. A. Parkos et al., *J. Clin. Invest.* 88, 1605 (1991).
26. Allen-Vercoe et al., *J Med Microbiol* 48, 771-780 (1999).
27. Bardocz, S. et al., *Br J Nutr* 76, 613-626 (1996).
28. Bernet-Camard et al., *Appl Environ Microbiol* 63, 2747-2753 (1997).
29. Bovee-Oudenhoven et al., *Gastroenterology* 113, 550-557 (1997).
30. Bovee-Oudenhoven et al., *J Nutr* 129, 607-612 (1999).
31. Bry, L et al., *Science* 273, 1380-1383 (1996).
32. Bryant, M. P. *Am J Clin Nutr* 25, 1324-1328 (1972).
33. Carter, J Exp Med 139, 1189-1203 (1974).
34. Cebra, J. J., *Am J Clin Nutr* 69, 1046S-1051S (1999).
35. Chang, J. et al., *J Appl Bacteriol* 77, 709-718 (1994).
36. Collins, C. H. L. P. M. (1989) *Microbiological Methods* Butterworths, London.
37. Darwin, K. H. et al., *Clin Microbiol Rev* 12, 405-428 (1999).
38. Eaves-Pyles, T. et al., *J Immunol* 166, 1248-1260 (2001).
39. Ewen, S. W. et al., *FEMS Immunol Med Microbiol* 18, 185-192 (1997).
40. Filho-Lima, J. V. et al., *J Appl Microbiol* 88, 365-370 (2000).
41. Fleckenstein, J. M. et al., *J Clin Invest* 107, 27-30 (2001).
42. Friman, G. et al., *Scand J Infect Dis* 16, 111-119 (1984).
43. Gewirtz, A. T. et al., *J Immunol* 167, 1882-1885 (2001).
44. Grant, G. (1996) Management of Animal Experiments. *COST 98. Effects of antinutrients on the nutritional value of legume diets* (Bardocz, S; Pusztai.A., ed) pp. 44-51, European Commision, Brussels.
45. Grant, G. et al., *Pancreas* 20, 305-312 (2000).
46. Havelaar, A. H. et al., *J Appl Microbiol* 91, 442-452 (2001).
47. Henderson, S. C. et al., *Infect Immun* 67, 3580-3586 (1999).
48. Henriksson et al., *J Appl Microbiol* 90, 223-228 (2001).
49. Herias et al., *Scand J Immunol* 48, 277-282 (1998).
50. Herias, M. V. et al., *Clin Exp Immunol* 116, 283-290 (1999).
51. Hooper, L. V. et al., *Proc Natl Acad Sci U S A* 96, 9833-9838 (1999).
52. Hooper, L. V. et al., *Curr Opin Microbiol* 3, 79-85 (2000).
53. Hooper, L. V. et al., *Glycobiology* 11, 1R-10R (2001).
54. Hooper, L. V. et al., *Science* 291, 881-884 (2001).
55. Hudault, S. et al., *Appl Environ Microbiol* 63, 513-518 (1997).
56. Hudault, S. et al., *Gut* 49, 47-55 (2001).
57. Isberg, R. R. et al., *Trends Microbiol* 8, 291-293 (2000).
58. Islam, A. F. et al., *Infect Immun* 68, 1-5 (2000).
59. Isolauri, E. et al., *Am J Clin Nutr* 73, 444S-450S (2001).

60. Izadpanah, A. et al., *Am J Physiol Gastrointest Liver Physiol* 280, G710-G719 (2001).
61. Kellermann, S. A. et al., *J Immunol* 167, 682-690 (2001).
62. Kingsley, R. A et al., *Bacterial Invasion into Eukaryotic Cells* (Oelschlaeger, T. A. and Hacker, J., eds) pp. 321-342, Kluwer Academic/Plenum Publishers, New York (2000).
63. Klasing, K. C. C. C. C. *Protein Metabolism and Nutrition* (Lobely, G. E; Wnite, A. and MacRae, J. C., eds) pp. 253-264, Wageningen Pers, Wageningen (1999).
64. Lang, C. H. et al., *Am J Physiol Endocrinol Metab* 278, E1133-E1143 (2000).
65. Lopez-Boado, Y. S. et al., *J Cell Biol* 148, 1305-1315 (2000).
66. Lu, L. et al., *Am J Clin Nutr* 73, 1124S-1130S (2001).
67. Lu, S. et al., *Infect Immun* 67, 5651-5657 (1999).
68. Madara, J. L. *Aliment Pharmacol Ther* 11 Suppl 3, 57-62 (1997).
69. Maia, O. B. et al., *Vet Microbiol* 79, 183-189 (2001).
70. McCormick, B. A. et al., *J Cell Biol* 131, 1599-1608 (1995).
71. Miles, A. A. et al., *J Hyg* 38, 749 (1993).
72. Naughton, P. J. et al., *FEMS Immunol Med Microbiol* 12, 251-258 (1995).
73. Naughton, P. J. et al., *J Appl Bacteriol* 81, 651-656 (1996).
74. Naughton, P. J. et al., *J Med Microbiol* 50, 191-197 (2001).
75. Netea, M. G. et al., *J Immunol* 164, 2644-2649 (2000).
76. Noack, J. et al., *J Nutr* 130, 1225-1231 (2000).
77. Pier, G. B. et al., *Infect Immun* 60, 4768-4776 (1992).
78. Rescigno, M. et al., *Nat Immunol* 2, 361-367 (2001).
79. Salminen, S. et al., *Br J Nutr* 80 Suppl 1, S147-S171 (1998).
80. Scharek, L. et al., *Immunobiology* 202, 429-441 (2000).
81. Schechter, L. M. et al., *Bacterial Invasion into Eukaryotic Cells*. (Oelschlaeger, T. A. H. J., ed) pp. 289-320, Kluwer Academic/Plenum Publishers, New York (2000).
82. Shu, Q. et al., *Med Microbiol Immunol (Berl)* 189, 147-152 (2001).
83. Silva, A. M. et al., *J Appl Microbiol* 86, 331-336 (1999).
84. Snel, J. et al., *Can J Microbiol* 44, 1177-1182 (1998).
85. Stucchi, A. F. et al., *Am J Physiol Gastrointest Liver Physiol* 279, G1298-G1306 (2000).
86. Talham, G. L. et al., *Infect Immun* 67, 1992-2000 (1999).
87. Teng, L. J. et al., *J Clin Microbiol* 38, 1672-1675 (2000).
88. Van Der Waaij, D. *The Germ-free Animal in Biomedical Research* (Coates, M. E. Gustafsson, .B. E., ed) pp. 155-165, Laboratory Animals Ltd, London (1984).
89. Vassiloyanakopoulos, A. P. et al., *Proc Natl Acad Sci U S A* 95, 7676-7681 (1998).
90. Vazquez-Torres, A. et al., *Nature* 401, 804-808 (1999).
91. Yurdusev, N. et al., *Can J Microbiol* 33, 226-231 (1987).
92. Yurdusev, N. et al., *Infect Immun* 57, 724-731 (1989).
93. Zimmerman, B. J. et al., *Am J Physiol* 259, H390-H394 (1990).

The invention claimed is:

1. A method of treating inflammatory response of intestinal cells in a mammal afflicted with an inflammatory disease of the bowel, said inflammatory response being caused by NF-κB-induced inflammatory cytokines, said method comprising the step of administering to the subject a composition comprising as the only bacterial anti-inflammatory active ingredient a therapeutically effective dose of *Bacteroides thetaiotaomicron*.

2. The method of claim 1, wherein said *Bacteroides thetaiotaomicron* are administered live to the subject by means of a foodstuff or suppository.

3. The method of claim 1, wherein said inflammatory disease of the bowel is Crohn's disease.

4. The method of claim 1, wherein the therapeutically effective dose of *Bacteroides thetaiotaomicron* is delivered orally.

5. The method of claim 1, wherein transcriptional activity of NF-κB is altered in the subject by enhanced nuclear export of the NF-κB.

6. The method of claim 1, wherein an amount of PPARγ/RelA complexes in the cell cytosol of the subject is increased.

7. The method of claim 1, wherein said inflammatory response is determined through measurement of the levels of one or more cytokines selected from the group consisting of TNF-α, IL-8, MIP-2α and Cox-2.

* * * * *

SEQUENCE LISTING

```
<160> NUMBER OF SEQ ID NOS: 4

<210> SEQ ID NO 1
<211> LENGTH: 22
<212> TYPE: DNA
<213> ORGANISM: Artificial Sequence
<220> FEATURE:
<223> OTHER INFORMATION: probe for NF-kB consensus binding sequence

<400> SEQUENCE: 1
agttgagggg actttcccag gc                                              22

<210> SEQ ID NO 2
<211> LENGTH: 21
<212> TYPE: DNA
<213> ORGANISM: Artificial Sequence
<220> FEATURE:
<223> OTHER INFORMATION: probe for AP-1 consensus binding sequence

<400> SEQUENCE: 2
cgcttgatga gtcagccgga a                                               21

<210> SEQ ID NO 3
<211> LENGTH: 22
<212> TYPE: DNA
<213> ORGANISM: Artificial Sequence
<220> FEATURE:
<223> OTHER INFORMATION: BTH forward primer

<400> SEQUENCE: 3
tggagtttta ctttgaatgg ac                                              22

<210> SEQ ID NO 4
<211> LENGTH: 18
<212> TYPE: DNA
<213> ORGANISM: Artificial Sequence
```

```
<220> FEATURE:
<223> OTHER INFORMATION: BTH reverse primer

<400> SEQUENCE: 4
ctgccctttt acaatggg                                                    18
```